United States Patent [19]
Vacanti et al.

[11] Patent Number: 5,759,830
[45] Date of Patent: *Jun. 2, 1998

[54] THREE-DIMENSIONAL FIBROUS SCAFFOLD CONTAINING ATTACHED CELLS FOR PRODUCING VASCULARIZED TISSUE IN VIVO

[75] Inventors: Joseph P. Vacanti, Winchester; Robert S. Langer, Somerville, both of Mass.

[73] Assignees: Massachusetts Institute of Technology; Children's Medical Center Corporation, both of Boston, Mass.

[*] Notice: The term of this patent shall not extend beyond the expiration date of Pat. No. 5,567,712.

[21] Appl. No.: 203,522

[22] Filed: Feb. 28, 1994

Related U.S. Application Data

[63] Continuation of Ser. No. 679,177, Mar. 26, 1991, abandoned, which is a continuation of Ser. No. 401,648, Aug. 30, 1989, abandoned, which is a continuation of Ser. No. 123,579, Nov. 20, 1987, abandoned, which is a continuation-in-part of Ser. No. 933,018, Nov. 20, 1986, abandoned.

[51] Int. Cl.$^6$ .............................. C12N 11/08; C12N 5/00; C12N 5/22
[52] U.S. Cl. .................. 435/180; 424/93.7; 435/398; 435/400; 435/402
[58] Field of Search .................. 435/174, 175, 435/177, 180, 398, 400, 402; 424/93.7

[56] References Cited

U.S. PATENT DOCUMENTS

| | | | |
|---|---|---|---|
| 3,992,725 | 11/1976 | Homsy | 623/11 |
| 4,026,304 | 5/1977 | Levy | 128/419 |
| 4,060,081 | 11/1977 | Yannas | 128/156 |
| 4,192,827 | 3/1980 | Mueller et al. | 525/123 |
| 4,239,664 | 12/1980 | Teng et al. | 260/17.4 R |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 435/240.23 |
| 4,328,204 | 5/1982 | Wasserman | 424/486 |
| 4,427,808 | 1/1984 | Stol et al. | 524/24 |
| 4,431,428 | 2/1984 | Schmer | 604/897 |
| 4,438,198 | 3/1984 | Schmer | 435/178 |
| 4,444,887 | 4/1984 | Hoffmann | 435/240 |
| 4,446,234 | 5/1984 | Russo et al. | 435/29 |
| 4,450,150 | 5/1984 | Sidman | 424/1.1 |
| 4,456,687 | 6/1984 | Green | 435/240.25 |
| 4,458,678 | 7/1984 | Yannas | 428/155 |
| 4,483,329 | 9/1982 | Chapman | 260/403 |
| 4,485,096 | 11/1984 | Bell | 424/95 |
| 4,485,097 | 11/1984 | Bell | 424/95 |
| 4,489,056 | 12/1984 | Himmelstein | 424/22 |
| 4,505,266 | 3/1985 | Yannas et al. | 128/898 |
| 4,520,821 | 6/1985 | Schmidt | 435/240.21 |
| 4,528,265 | 7/1985 | Becker | 435/172.1 |
| 4,544,516 | 10/1985 | Hughes et al. | 264/108 |
| 4,545,082 | 10/1985 | Hood | 623/12 |
| 4,553,272 | 11/1985 | Mears | 623/1 |
| 4,559,304 | 12/1985 | Kusai et al. | 435/240.43 |
| 4,563,489 | 1/1986 | Vrist | 524/21 |
| 4,563,490 | 1/1986 | Stol et al. | 524/24 |
| 4,576,608 | 3/1986 | Homsy | 623/13 |
| 4,645,669 | 2/1987 | Reid | 435/240.43 |
| 4,713,070 | 12/1987 | Mano | 623/12 |
| 4,886,870 | 12/1989 | D'Amore et al. | 528/206 |
| 4,888,176 | 12/1989 | Langer et al. | 424/426 |
| 4,891,225 | 1/1990 | Langer et al. | 424/428 |
| 4,963,489 | 10/1990 | Naughton et al. | 435/249.1 |
| 5,041,138 | 8/1991 | Vacantriest | 623/16 |

FOREIGN PATENT DOCUMENTS

| | | |
|---|---|---|
| 2853614 | 7/1979 | Germany. |

OTHER PUBLICATIONS

Vacant, et al. J. Pedatric Surgery 23(1) 3–9 1988.
Leong et al. J. Biomedical Materials Research, 19:941–955, 1985.
Kretschmer, et al., Ann. Surg. 187, 79–86 (1978).
Naji, et al., Surgery 86, 218–226 (1979).
Sutherland, et al., Surgery, 83, 124–132 (1977).
Sommer, et al., Transplant Proc. 11, 578–584 (1979);
Groth, et al., Transplant Proc. 9, 313–316 (1977).
Matas, et al., Science 192, 892–894 (1976).
Ebata, et al., Surg. Forum 29, 338–340 (1978).
Seldon, et al., Transplant 38, 81–83 (1984).
Kusano, et a., Acta Japoni Hepato 63, 345–351 (1989).
Minato, et al., Euro. Surg. Res. 16, 162–169 (1984).
Vroeman, et al., Transplantation 42, 130–135 (1986).
Strom, et al., JNCI 68, 771–778 (1982).
Freshney "The Culture Environment:I. Substrate, Gas Phase and Temperature" in Culture of Animal Cells, pp. 55–66 (Alan R. Liss, NY 1983).
Yannas, et al., Science 215, 174–176 (1982).

(List continued on next page.)

Primary Examiner—David M. Naff
Attorney, Agent, or Firm—Arnall Golden & Gregory

[57] ABSTRACT

A cell-scaffold composition is prepared in vitro for implanting to produce functional organ tissue in vivo. The scaffold is three-dimensional and is composed of fibers of a biocompatible, biodegradable, synthetic polymer. Cells derived from vascularized organ tissue are attached in vitro to the surface of the fibers uniformly throughout the scaffold in an amount effective to produce functional vascularized organ tissue in vivo. Fibers of the scaffold are spaced apart such that the maximum distance over which diffusion of nutrients and gases must occur through a mass of cells attached to the fibers is between 100 and 300 microns. The diffusion provides free exchange of nutrients, gases and waste to and from cells proliferating throughout the scaffold in an amount effective to maintain cell viability throughout the scaffold in the absence of vascularization. Cells attached to the fibers may be lymphatic vessel cells, pancreatic islet cells, hepatocytes, bone forming cells, muscle cells, intestinal cells, kidney cells, blood vessel cells, thyroid cells or cells of the adrenal-hypothalamic pituitary axis. Hollow or solid fibers are made from a polyanhydride, polyorthoester, polyglycolic acid or polymethacrylate, and the fibers may have a coating which enhances cell attachment.

22 Claims, 14 Drawing Sheets

OTHER PUBLICATIONS

Yannas, et al., *Polym. Prepr. Am. Chem. Soc. Div. Polym. Chem.* 16(2), 209–214 (1975).

Yannas, et al., *J. Biomed. Mater. Res.* 14, 65–81 (1980).

Jaksie, et al., *Ann. Rev. Med.* 38, 107 (1987).

Burke, *The Role of Extracellular Matrix in Development* 351–355 (Alan R. Liss, Inc., NY 1984).

Yannas, et al., *Iss. Polym. Biomaterial* 106, 221–220 (1986).

Yannas, *J. of Trauma* 24(9), S29–S39 (1984).

Yannas, et al., *Polym. Sci. Technol. Iss. Adv. Biomed. Polymer* 35, 1–9 (Plenum 1987).

Yannas, et al., *Polym. Material Sci. Eng.* 53, 216–218 (1985).

Cosimi, et al., *Surgical Clinics of N.A.* 58(2), 435–451 (1978).

Jones, et al., *Cancer Invasion and Metastasis: Biologic and Therapeutic Aspects* pp. 177–185 (Raven Press, NY 1984).

Schubert, et al., *J. Cell Biol.* 104, 635–643 (1987).

Thuroff et al., *Urology* 21(2), 155–158 (1983).

Bazeed et al., *Urology* 21(5), 501–504 (1983).

Mounzer et al., *Urology* 28 (2), 127–130 (1986).

Bazeed et al., Urology 21(1), 53–57 (1983).

Culliton, Science, 246:748, 1989.

Fieshney, Animal Cell Culture: A Practical Approach. IRL Press Co., 1986, pp. 179–180.

Thompson, Science, 258:744–746, 1992.

Schneck Jr New York Times p. 63.

Thurff et al Virology 21 155–158 1983.

Structure & fucntion in Man WB Sounded Co. 1982 pp. 85–88, 383, 384, 413, 484 & 504–507.

Leeson et al. WB Saunders Co. 1976 pp. 86, 87, 88.

Polyglactin 910 (Vicryl)

Polyorthoester

Polyanhydride

Nutrition Diffusion Experiment

THREE-DIMENSIONAL FIBROUS SCAFFOLD CONTAINING ATTACHED CELLS FOR PRODUCING VASCULARIZED TISSUE IN VIVO

This is a continuation of U.S. patent application Ser. No. 07/679,177 filed Mar. 26, 1991, now abandoned, which is a continuation of U.S. patent application Ser. No. 07/401,648 filed Aug. 30, 1989, now abandoned, which is a continuation of U.S. patent application Ser. No. 07/123,579 filed Nov. 20, 1987, now abandoned, which is a continuation in part of U.S. patent application Ser. No. 06/933,018 filed Nov. 20, 1986, now abandoned.

The United States Government has rights in this invention by virtue of NIH grant No. 6M 26698.

BACKGROUND OF THE INVENTION

This invention is generally in the field of medicine and cell culture, and in particular in the area of implantable organs formed on biocompatible artificial matrices.

Loss of organ function can result from congenital defects, injury or disease.

One example of a disease causing loss of organ function is diabetes mellitus. Diabetes mellitus destroys the insulin producing beta cells of the pancreas. As a consequence, serum glucose levels rise to high values because glucose cannot enter cells to meet their metabolic demands. Through a complex series of events, major problems develop in all systems secondary to the vascular changes which occur. The current method of treatment consists of the exogenous administration of insulin, which results in imperfect control of blood sugar levels. The degree of success in averting the complications of diabetes remains controversial.

A recent and still experimental approach has been the transplantation of pancreatic tissue, either as a whole organ or as a segment of an organ, into the diabetic patient. Serum glucose appears to be controlled in a more physiological manner using this technique and the progression of complications is thereby slowed. An earlier approach which was not successful in achieving long-term benefits was the transplantation of isolated islet cells through injection of isolated clusters of islet cells into the portal circulation, with implantation in the vascular bed of the liver. More recent experimental methods have included encapsulation of pancreatic beta cells to prevent immune attack by the host and injection of fetal beta cells beneath the capsule of the kidney. Although there is evidence of short term function, long term results have been less satisfactory (D. E. R. Sutherland, *Diabetologia* 20, 161–185 (1981); D. E. R. Sutherland, *Diabetologia* 20, 435–500 (1981)). Currently whole organ pancreatic transplantation is the preferred treatment.

There are also many diseases which cause significant scarring of the liver, ultimately causing hepatic failure. There are no artificial support systems for liver failure, so that, in the absence of a successful transplant, liver failure always results in the death of the patient. It has been estimated that 30,000 people die of hepatic failure every year in the United States, at a cost to society of $14 billion dollars annually.

There are many diseases which are termed "inborn errors of metabolism", including genetic defects that result in defects of protein metabolism, defects of amino acid metabolism, defects of carbohydrate metabolism, defects of pyrimidine and purine metabolism, defects of lipid metabolism, and defects of mineral metabolism. A large number of these diseases are based in defects within the liver itself. Many of these patients have a structurally normal liver or reasonably normal liver at the time diagnosis is made. Many of the diseases, in fact, do not damage the native liver, rather, the damage occurs in other organs, such as the central nervous system.

The usual indications for liver transplantation include acute fulminant hepatic failure, chronic active hepatitis, biliary atresia, idiopathic cirrhosis, primary biliary cirrhosis, sclerosing cholangitis, inborn errors of metabolism, some forms of malignancy, and some other rare indications. The only method for treating these patients is to maintain them until a liver becomes available for transplantation. Transplantation of the whole liver has become an increasingly successful surgical manipulation through the 1980's, largely through the efforts of Dr. Thomas Starzl. However, the technical complexity of the surgery, the enormous loss of blood, the stormy postoperative course, and the many unknowns of hepatic transplantation, have made it an expensive technology available only in major medical centers. It has become increasingly clear that because of donor scarcity, transplantation will never meet the needs of the patients who require it. Currently, approximately 600 patients per year undergo hepatic transplantation. Even if that capacity were tripled, it would fall short of the 30,000 patients dying of end-stage liver disease. There currently does not exist good artificial hepatic support for patients awaiting transplantation.

Another group of patients suffering from liver disease are those with alcohol induced liver disease. Currently, patients with end-stage liver disease from alcohol use do not have access to transplantation. There are several reasons for this including scarcity of donor organs and noncompliance with complex care. In the U.S. alone, this patient population is very large. For example, in the Baltimore area during 1973 the age adjusted incidence rates for all alcoholic liver diseases per 100,000 population over 20 years were: 36.3 for white males, 19.8 for white females, 60.0 for nonwhite males, and 25.4 for nonwhite females. The morbidity for liver cirrhosis has been reported to be twenty-eight times higher among serious problem drinkers than amongst non-drinkers in a survey of factory workers. There is a direct correlation between the amount of alcohol consumed and the incidence of cirrhosis. The mortality rates for cirrhosis vary greatly from country to country, ranging from 7.5 per 100,000 in Finland to 57.2 per 100,000 in France. In the U.S., the trend has been alarming in terms of increasing incidence of alcoholic cirrhosis and death. Between 1950 to 1974, deaths from cirrhosis in the U.S. increased by 71.7% while deaths from cardiovascular diseases decreased by 2%. At this time, these patients have no options.

There are many other vital organ systems for which there is no adequate means for replacement or restoration of lost function. For example, in the past, loss of the majority of intestine was a fatal condition. Although patients can now be supported totally with nutrition supplied via the veins, this is thought of as a "half-way technology" because of the many complications associated with this technique. One problem is that, over time, many patients on total parenteral nutrition develop irreversible liver disease and die of their liver disease. Other patients develop severe blood stream infections requiring multiple removal and replacement procedures. They may eventually lose all available veins and succumb of malnutrition or die of infection.

Intestinal transplantation has been unsuccessful to date because of major biological problems due to the large numbers of lymphocytes in the intestine which are transferred to the recipients. These may produce an immunologic reaction termed "graft vs. host" disease, in which the lymphocytes from the transplanted intestine attack and eventually kill the patient.

Diseases of the heart and muscle are also a major cause of morbidity and mortality in this country. Cardiac transplantation has been an increasingly successful technique where heart muscle has failed, but, as in the case of liver transplants, requires a donor and the use of strong immunosuppressant drugs.

The emergence of organ transplantation and the science of immunobiology has allowed replacement of the kidney, heart, liver, and other organs. However, as the ability to perform these complex operations has improved, the limitations of the technology have become more evident. For example, in pediatric liver transplantation, donor scarcity has increased as more programs have opened. Only a small number of donors are available in the U.S. for 800–1,000 children/year in liver failure and those children that undergo transplantation are often so ill by the time a liver is found that the likelihood of success is diminished. The surgery is complex and usually associated with major blood loss. The preservation time is short and, therefore, results in major logistical problems in matching a distant donor with a recipient. For these reasons, the undertaking is expensive and labor intensive, requiring a major investment of resources available only in tertiary care facilities.

Selective cell transplantation of only those parenchymal elements necessary to replace lost function has been proposed as an alternative to whole or partial organ transplantation (P. S. Russell, *Ann. Surg.* 201(3),255–262 (1985)). This has several attractive features, including avoiding major surgery with its attendant blood loss, anesthetic difficulties, and complications. It replaces only those cells which supply the needed function and, therefore, problems with passenger leukocytes, antigen presenting cells, and other cell types which may promote the rejection process are avoided. Adding the techniques of cell culture provides another set of tools to aid in the transplantation process. The ability to expand cell numbers with proliferation of cells in culture, in theory, allows autotransplantation of one's own tissue. For example, hepatocyte injections into the portal circulation have been attempted to support hepatic function. A recent novel approach in which hepatocytes were attached to collagen coated microcarrier beads prior to injection into the peritoneal cavity demonstrated successful implantation, viability of the implanted hepatocytes, and function, as described by A. A. Demetriou.et al., *Science* 233,1190–1192 (1986).

Loss of other types of organ or tissue function such as muscle or nervous tissue can also lead to deforming illnesses and social tragedies. Methods of muscle and nerve transfer have been developed by surgeons through the last fifty years which are ingenious in design. An example of a technique for restoring nerve function has been to string dead nerve fibers from nerve centers to places with lost nerve function. Many other disorders of the nervous system have eluded adequate medical therapy. Recently, nerve cell transplantation has been proposed as a treatment modality in certain degenerative diseases of the nervous system such as Parkinson's disease and Alzheimer's disease. Autotransplantation of the adrenal tissue or injection of fetal cell suspensions into the brain appears to be of benefit. Loss, deformation or obstruction of blood vessels is another frequent cause of disease, such as high blood pressure or aneurysm. In the past, surgeons have primarily dealt with this problem by grafting blood vessels from another portion of the body to the affected area or by implanting cloth substitutes as permanent replacements. Disadvantages include the requirement of multiple operations as well as the associated pain to the patient.

Even though these techniques do not have many of the problems associated with transplantation of organs such as the liver or intestine, the results are still often imperfect.

Although different from organs such as the liver and interesting in a number of ways, skin is also an organ subject to damage by disease or injury which performs the vital role of protecting the body from fluid loss and disease. Although skin grafts have been prepared from animal skin or the patient's skin, more recently "artificial skin" formed by culturing epidermal cells has been utilized.

One method for forming artificial skin is by seeding a fibrous lattice with epidermal cells. For example, U.S. Pat. No. 4,485,097 to Bell discloses a hydrated collagen lattice which, in combination with contractible agents such as platelets and fibroblasts and cells such as keratinocytes, is used to produce a skin-equivalent. U.S. Pat. No. 4,060,081, to Yannas et al. discloses a multilayer membrane useful as synthetic skin which is formed from an insoluble non-immunogenic material which is nondegradable in the presence of body fluids and enzymes, such as cross-linked composites of collagen and a mucopolysaccharide, overlaid with a non-toxic material such as a synthetic polymer for controlling the moisture flux of the overall membrane. U.S. Pat. No. 4,458,678 to Yannas et al. discloses a process for making a skin-equivalent material wherein a fibrous lattice formed from collagen cross-linked with glycosaminoglycan is seeded with epidermal cells.

A disadvantage to the first two methods is that the matrix is formed of a "permanent" synthetic polymer. The '678 patent has a feature that neither of the two prior patents has, a biodegradable matrix which can be formed of any shape, using the appropriate cells to produce an organ such as the skin. Unfortunately, there is a lack of control over the composition and configuration of the latter matrices since they are primarily based on collagen. Further, since collagen is degraded by enzymatic action as well as over time by hydrolysis, the degradation is quite variable. Moreover, the matrix is completely infiltrated with cells and functional in the absence of the moisture controlling polymer overlay only when it is grafted onto the patient and capillaries have formed a vascular network through the entire thickness of the matrix. The limitation of these matrices as a function of diffusion is discussed in the article by Yannas and Burke in *J.Biomed.Mater.Res.*, 14, 65–81 (1980) at page 73. Although the authors recognized that the pore size and thickness of the matrix were controlling factors in determining viability and successful engraftment, their only ways of dealing with the lack of sufficient nutrient supply to the interior portions of the matrix at the time of engraftment were either to ignore the problem and hope the graft was thin enough and porous enough to allow sufficient capillary growth along with migration of the epithelial cells into the matrix, or to seed the graft with additional epithelial cells after sufficient capillary growth into the matrix had occurred.

Although skin is considered to be an "organ" of the body, these methods for making artificial skin have not been used to make other types of organs such as a liver or pancreas, despite the all encompassing statements in the patents that the disclosed or similar techniques could be utilized to do so. It is postulated that, when these methods are used to construct organs having a larger overall three dimensional structure, such as a liver or pancreas, the cells within the center of the organs tend to die after a period of time and that the initial growth rate is not maintained, in a manner analogous to the situation with very large tumors which are internally necrotic due to a decrease in diffusion of nutrients into the growing three-dimensional structure as the cell density and thickness increase. Indeed, in view of the Yannas and Burke article, it appears that growth within a matrix, even one as thin as a skin graft, presented problems until vascularization had occurred, even at relatively low cell densities.

It is therefore an object of the present invention to disclose a method and means for creating a variety of organs, including skin, liver, kidneys, blood vessels, nerves, and muscles, which functionally resemble the naturally occurring organ.

It is a further object of the present invention to provide a method and means for designing, constructing and utilizing artificial matrices as temporary scaffolding for cellular growth and implantation.

It is a still further object of the invention to provide biodegradable, non-toxic matrices which can be utilized for cell growth, both in vitro and in vivo, as support structures in transplant organs immediately following implantation.

It is another object of the present invention to provide a method for configuring and constructing biodegradable artificial matrices such that they not only provide a support for cell growth but allow and enhance vascularization and differentiation of the growing cell mass following implantation.

It is yet another object of the invention to provide matrices in different configurations so that cell behavior and interaction with other cells, cell substrates, and molecular signals can be studied in vitro.

SUMMARY OF THE INVENTION

The present invention is a method and means whereby cells having a desired function are grown on polymer scaffolding using cell culture techniques, followed by transfer of the polymer-cell scaffold into a patient at a site appropriate for attachment, growth and function, after attachment and equilibration, to produce a functional organ equivalent. Success depends on the ability of the implanted cells to attach to the surrounding environment and to stimulate angiogenesis. Nutrients and growth factors are supplied during cell culture allowing for attachment, survival or growth as needed.

After the structure is implanted and growth and vascularization take place, the resulting organoid is a chimera formed of parenchymal elements of the donated tissue and vascular and matrix elements of the host. The polymer scaffolding used for the initial cell culture is constructed of a material which degrades over time and is therefore not present in the chimeric organ. Vascular ingrowth following implantation allows for normal feedback mechanisms controlling the soluble products of the implanted cells.

The preferred material for forming the matrix or support structure is a biodegradable artificial polymer, for example, polyglycolic acid, polyorthoester, or polyanhydride, which is degraded by hydrolysis at a controlled rate and reabsorbed. These materials provide the maximum control of degradability, manageability, size and configuration. In some embodiments these materials are overlaid with a second material such as gelatin or agarose to enhance cell attachment. The polymer matrix must be configured to provide both adequate sites for attachment and adequate diffusion of nutrients from the cell culture to maintain cell viability and growth until the matrix is implanted and vascularization has occurred. The presently preferred structure for organ construction is a branched fibrous tree-like structure formed of polymer fibers having a high surface area. The preferred structure results in a relatively shallow concentration gradient of nutrients, wastes, and gases, so as to produce uniform cell growth and proliferation. Theoretical calculations of the maximum cell attachment suggest that fibers 30 microns in diameter and one centimeter in length can support 125,000,000 cells and still provide access of nutrients to all of the cells. Another advantage of the biodegradable material is that compounds may be incorporated into the matrix for slow release during degradation of the matrix. For example, nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, and drugs can be incorporated into the matrix or provided in conjunction with the matrix, in solution or incorporated into a second biodegradable polymer matrix.

Cells of one or more types can be selected and grown on the matrix. The matrix structure and the length of time and conditions under which the cells are cultured in vitro are determined on an individual basis for each type of cell by measuring cell attachment (only viable cells remain attached to the polymers), extent of proliferation, and percent successful engraftment. Examples of cells which are suitable for implantation include hepatocytes and bile duct cells, islet cells of the pancreas, parathyroid cells, thyroid cells, cells of the adrenal-hypothalmic-pituitary axis including hormone-producing gonadal cells, epithelial cells, nerve cells, heart muscle cells, blood vessel cells, lymphatic vessel cells, kidney cells, and intestinal cells, cells forming bone and cartilage, smooth and skeletal muscle.

Initially growing the cells in culture allows manipulation of the cells which may be beneficial following implantation of the matrix cell structure. Presently available technology allows the introduction of genes into the cells to make proteins which would otherwise be absent, such as those resulting from liver protein deficiencies and metabolic defects such as cystic fibrosis. Repression of gene expression may also be used to modify antigen expression on the cell surface, and thereby the immune response, so that cells are not recognized as foreign.

The present invention also provides techniques and matrices for in vitro studies. Although current methods of cell culture have provided valuable insight into fundamental aspects of cell organization and function, studies of cell behavior, communication, control, and morphogenesis have been difficult for lack of a system controllable in three dimensions. Artificial matrices which have been coated with attached cells can be embedded in extracellular matrices such as collagen, basement membrane complexes such as Matrigel™, or other materials. Various combinations of cell types, biochemical signals for growth, differentiation, migration, and extracellular matrix components can then be examined in vitro in a three-dimensional system. By controlling all of these elements, and watching behavior, the field of biomedical science may gain new insights into the actions of cells in a setting more closely resembling structure as it occurs in nature.

BRIEF DESCRIPTION OF THE DRAWINGS

FIG. 20b is an enlarged plan view of a spicule, as shown in FIG. 20a.

FIG. 21b is a graph of the collagen thickness (mm) versus number of cells surviving after 24 hours in the wells shown in FIG. 21a.

FIG. 22a shows cells from the control well after twenty-four hours, the cell number having doubled in twenty-four hours; FIG. 22b shows cells overlayed with 5.5 mm of 0.32% collagen, showing that the cell viability is markedly diminished and the cell number is far less than the initial plating number; and FIG. 22c shows cells overlayed with 12 mm of hydrated collagen placed between media and cells, showing that all of these cells are rounded and have died.

DETAILED DESCRIPTION OF THE DRAWINGS

Figure 1:
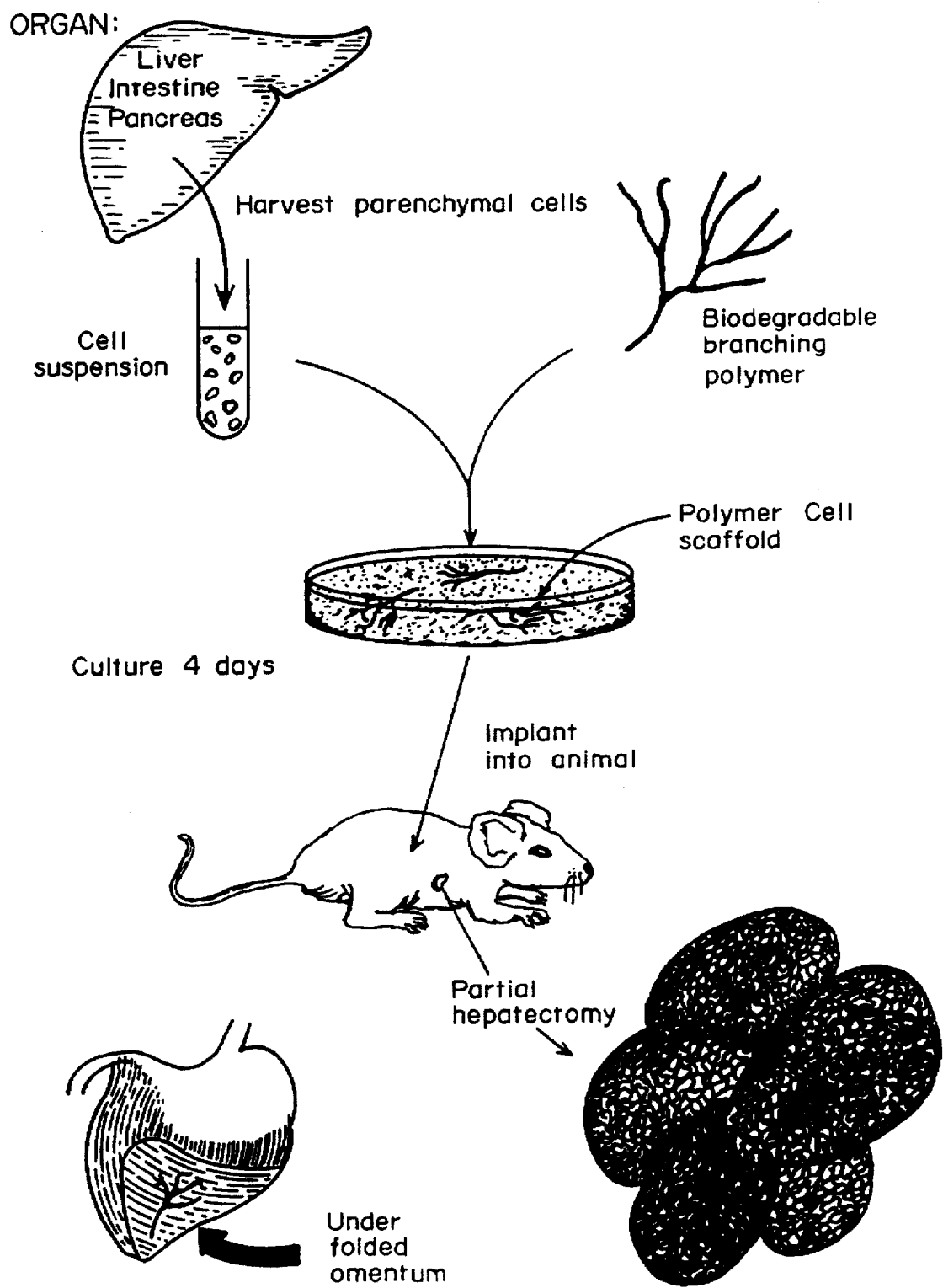
FIG. 1 is a schematic of the process of the present invention to produce a chimeric organ, in this diagram, a liver, pancreas or intestine: (1) the appropriate parenchymal cells are harvested, dispersed, and seeded onto the polymer matrix in cell culture, where attachment and growth occur and (2) a partial hepatectomy is performed to stimulate-growth of the transplant and the polymer-cell scaffold is then implanted into the recipient animal where neovascularization, cell growth, and reabsorption of the polymer matrix occurs.

The present invention is a method to provide functional organ equivalents using bioabsorbable artificial substrates as temporary scaffolding for cellular transfer and implantation. The success of the method depends on the integration of the following principles:

1. Every structure in living organisms is in a dynamic state of equilibrium, undergoing constant renewal, remodeling and replacement of functional tissue which varies from organ to organ and structure to structure.

2. Dissociated structural cells tend to reform structure, depending on the environment in which they are placed and the degree of alteration which they have undergone.

3. Tissue cannot be implanted in volumes greater than approximately one to three $mm^3$, because nutrition is supplied by diffusion until new blood vessels form, and this distance is the maximum distance over which diffusion can transpire until anqiogenesis occurs.

4. Cell shape is determined by cytoskeletal components and attachment to matrix plays an important role in cell division and differentiated function. If dissociated cells are placed into mature tissue as a suspension without cell attachment, they may have a difficult time finding attachment sites, achieving polarity, and functioning because they begin without intrinsic organization. This limits the total number of implanted cells which can remain viable to organize, proliferate, and function.

The latter principle is a key point in the configuration of the support matrices. For an organ to be constructed in tissue culture and subsequently successfully implanted, the matrices must have sufficient surface area and exposure to nutrients such that cellular growth and differentiation can occur prior to the ingrowth of blood vessels following implantation. After implantation, the configuration must allow for diffusion of nutrients and waste products and for continued blood vessel ingrowth as cell proliferation occurs.

This method for replacing or supplementing lost organ function has a number of advantages over either pharmacologic manipulation or transplantation of whole organs or parts of organs. Although great strides have been made in these areas, the results of these efforts are often deficient. Success in transplantation or pharmacologic manipulation may modify the outcome of a disease, but it usually does not result in cure, or it trades the original disease for the complications of non-specific immunosuppression.

One advantage of the present method is that it provides a means for selective transplantation of parenchymal cells which possess the necessary biologic function, without transplantation of passenger leukocytes and antigen-presenting cells. The result is greatly reduced risk of rejection of tissue without the use of drugs, especially if one is able to culture cells of the same or similar HLA tissue type. The present invention has another advantage over other means for treating organ function loss since the cells may be manipulated while in culture to introduce new genes to make absent protein products or modified to repress antigen expression on the cell surfaces so that immunosuppression is not needed when cells of the same HLA tissue type are not available. For example, a gene for insulin can be inserted into the patient's own deficient Islet cells. Other conditions can be corrected by insertion of the genes correcting Factor VIII deficiency, OTC deficiency, and disorders of carbohydrate and lipid metabolism. Techniques for the isolation, cloning and manipulation of these genes are available to those skilled in the art of genetic engineering.

The prospect of culturing the recipient's own cells for implantation has a further, more fundamental advantage: the elimination of the need for organ donors. For example, if a patient has lost 90% of his intestine because of ischemic damage, cells from the remaining 10% can be harvested and cultured. The cells expand in a logarithmic fashion in culture. The cells are cultured until suitable numbers of cells are achieved, the cells are grown onto the appropriate polymer scaffold, and placed back into the patient, to be allowed to vascularize, grow and function as a neointestine.

In the case of liver function replacement, it may be possible to construct a cell-matrix structure without the absolute need for hepatocyte proliferation in culture. This hypothesis is based on the observation that a high yield of hepatocytes can be obtained from a small piece of liver. For example, in experiments on 250 gm rats, it is known that the liver weighs approximately 12 gm. At a 90% viability rate this yields $2.5 \times 10^8$ viable hepatocytes. It is also thought that only 10% of hepatic cell mass is necessary for cell function. Therefore, for a 250 gm rat, 1.2 gm of tissue is needed, an implant of approximately $2.5 \times 10^7$ cells. This assumes no proliferation in vivo. Implants into children as well as adults are theoretically possible. An 8 month child has a normal liver that weighs approximately 250 gm. That child would, therefore, need 25 gm of tissue from a biopsy from a parent. An adult liver weighs-approximately 1500 gm, therefore, the biopsy would only be about 1.5% of his liver or $5.0 \times 10^8$ cells. Again, this assumes no proliferation. An adult would need a larger biopsy which would yield about $2.5 \times 10^9$ cells. If these cells are attached with high efficiency and implanted, proliferation in the new host should occur. The resulting hepatic cell mass should be adequate to replace needed function.

In distinct contrast to the prior art, the present method uses a temporary scaffolding for controlled growth and proliferation of cells in vitro, followed by implantation of functional cells into patients. The result is an organ which is vascularized in vivo to allow growth of the cells in a three-dimensional configuration similar to that of the organ whose function they are replacing. Both the design and construction of the scaffolding, as well as the conditions of the initial cell culture, are used to encourage cells to achieve their biological potential and replicate the ontogeny of organ formation which occurs in embryonic and fetal life. As described herein, this technique is termed chimeric neomorphogenesis.

The design and construction of the scaffolding is of primary importance. The matrix should be shaped to maximize surface area to allow adequate diffusion of nutrients and growth factors to the cells. The maximum distance over which adequate diffusion through densely packed cells can occur appears to be in the range of approximately 100 to 300 microns under conditions similar to those which occur in the body, wherein nutrients and oxygen diffuse from blood vessels into the surrounding tissue. The actual distance for each cell type and polymer structure must be determined empirically, measuring cell viability and function in vitro and in vivo. This determination for bovine capillary endothelial cells in combination with a collagen matrix will be described in detail in a subsequent example.

The cells are initially cultured using techniques known, to those skilled in the art of tissue culture. Once the cells have begun to grow and cover the matrix, they are implanted in a patient at a site appropriate for attachment, growth and function. One of the advantages of a biodegradable polymeric matrix is that angiogenic and other bioactive compounds may be incorporated directly into the matrix so that they are slowly released as the matrix degrades in vivo. As the cell-polymer structure is vascularized and the structure degrades, the cells will differentiate according to their inherent characteristics. For example, cells which would normally form tubules within the body will shape themselves into structures resembling tubules and nerve cells will extend along an appropriately constructed pathway.

Figure 2:
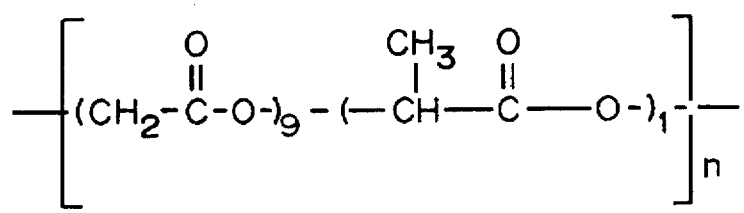
FIG. 2 are the chemical structures of polymers which have been used for biodegradable cellular matrices: (a) polygalactin; (b) polyorthoester; and (c) polyanhydride.
Figure 2:
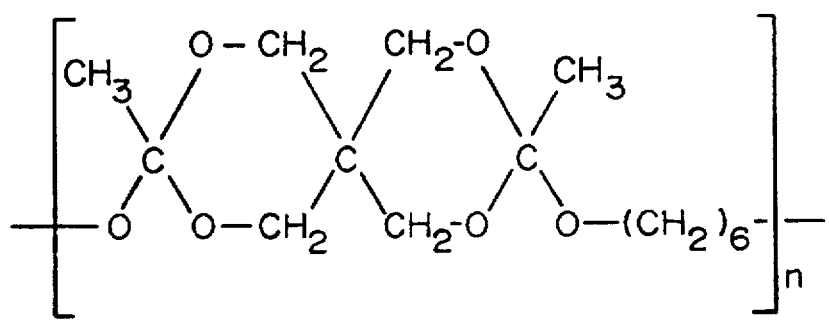
Figure 2:
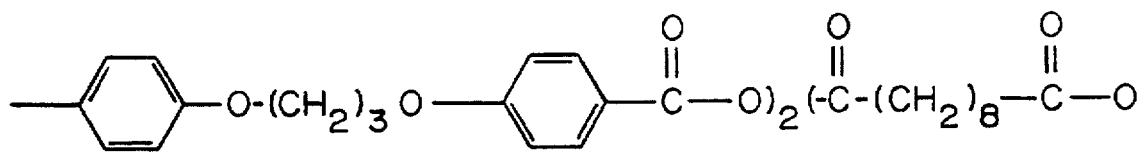

In the preferred embodiment, the matrix is formed of a bioabsorbable, or biodegradable, synthetic polymer such as a polyanhydride, polyorthoester, or polyglycolic acid, the structures of which are shown in FIG. 2. In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, mixtures thereof, and other materials known to those skilled in the art of cell culture. For in vitro studies, non-biodegradable polymer materials can be used, depending on the ultimate disposition of the growing cells, including polymethacrylate and silicon polymers. A non-degradable material is particularly useful when the cells are grown in culture for purposes other than transplantation, as in understanding cell to cell interaction: behavior, communication, control, and morphogenesis, since the preferred matrix structure allows for a higher immobilized cell density than can normally be achieved where nutrients are supplied solely by diffusion.

All polymers for use in the present invention must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies.

In vitro cell attachment and viability can be assessed using scanning electron microscopy, histology, and quantitative assessment with radioisotopes.

The configuration of the polymer scaffold must have enough surface area for the cells to be nourished by diffusion until new blood vessels interdigitate with the implanted parenchymal elements to continue to support their growth, organization, and function. Polymer discs seeded with a monolayer of cells, and branching fiber networks both satisfy these needs.

At the present time, a fibrillar structure is preferred. The fibers may be round, scalloped, flattened, star shaped, solitary or entwined with other fibers. The use of branching fibers is based upon the same principles which nature has used to solve the problem of increasing surface area proportionate to volume increases. All multicellular organisms utilize this repeating branching structure. Branching systems represent communication networks between organs as well as the functional units of individual organs. Seeding and implanting this configuration with cells allows implantation of large numbers of cells, each of which is exposed to the environment of the host, providing for free exchange of nutrients and waste while neovascularization is achieved.

Figure 3:
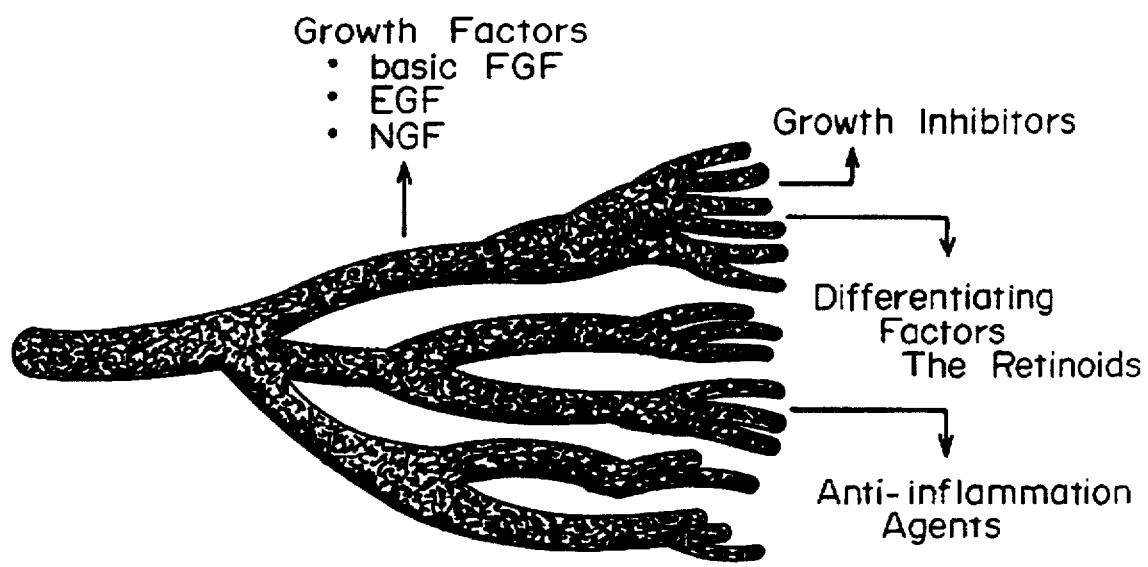
FIG. 3 is a diagram demonstrating the slow release of biologically active factors from the polymer matrix.

The method of the present invention is diagramed in FIG. 1. Cells 10 of the type required to provide the desired organ function are obtained from a donor, the recipient, or a cell culture line. A suspension 12 of, for example, liver, intestine, or pancreatic cells is prepared and seeded onto the polymer matrix 14. The cell-polymer scaffold 16 is cultured for an appropriate time under optimized conditions. The cell-polymer scaffold 16 is then implanted. In the example of an organ to provide lost liver function, the organ is implanted into the omentum adjacent the portal circulation which serves as a source of neovascularization. Optionally, partial hepatectomy is performed to stimulate cell regeneration. In addition to providing an adequate blood supply, "hepatotrophic" factors from the portal circulation aid in hepatic regeneration. It is also thought that factors such as insulin from the pancreatic blood supply specifically aid in the regenerative process. Alternatively, these factors, including nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix, as diagramed in FIG. 3.

The branching fibers 14 shown in FIG. 1, when 30 microns in diameter and 1.0 cm in length, can theoretically support 125,000,000 cells. In the example in which a liver organ is constructed, the cell populations can include hepatocytes and bile duct cells. Cells may be derived from the host, a related donor or from established cell lines. Fetal cells lines may be utilized since these cells are generally more hardy than other cell lines.

In one variation of the method using a single matrix for attachment of one or more cell lines, the scaffolding is constructed such that initial cell attachment and growth occur separately within the matrix for each population. Alternatively, a unitary scaffolding may be formed of different materials to optimize attachment of various types of cells at specific locations. Attachment is a function of both the type of cell and matrix composition.

Although the presently preferred embodiment is to utilize a single cell-matrix structure implanted into a host, there are situations where it may be desirable to use more than one cell-matrix structure, each implanted at the most optimum time for growth of the attached cells to form a functioning three-dimensional organ structure from the different cell-matrix structures. In some situations, it may be desirable to prepare the implantation site by initially exposing the cells at the site to a biodegradable polymer matrix including compounds or "de-differentiators" which induce a revision of the surrounding mesenchymal cells to become more embryonic. The-implanted cell matrix structure may then develop more normally in the fetal environment than it would surrounded by more mature cells.

Applying the above-described techniques and materials to the design, construction and implantation of a functional liver-type organ, one would begin with long, solid fibers seeded with bile duct epithelial cells inserted into a structure seeded with hepatocytes. After implantation and degradation of the polymer, the bile duct cells would form the appropriate connections for delivery of the bile to the desired locations. Ingrowth of the vascular supply, lymphatic network and nerve fibers could be encouraged. The combination polymer-cell scaffold with both attached hepatocytes and biliary epithelial cells could be implanted into a retroperitoneal position behind the mesocolon. An extension of the biliary conduit can be tunneled through the mesocolon and into a limb of jejunum so that biliary drainage can enter into the jejunum or upper intestine. As vascularization, cell-cell reorganization and polymer resorption occur, hepatic function should be replaced and bile flow should commence and proceed into the intestine. This location has several potential advantages because of its vascular supply. It is known that "hepatotrophic" factors come from the portal circulation and supply the liver for regeneration. Angiogenesis may occur from the portal bed immediately adjacent to the pancreas, a known source of hepatotrophic factors, as the inflow to these implanted hepatocytes. The outflow may be through retroperitoneal collatorals that drain into the systemic circulation through the hemiazygous system. If this occurs, there would be portosystemic channels through the implanted hepatic cells which may allow for decompression of portal hypertension, a complication leading to gastrointestinal bleeding in patients with end-stage liver disease.

In the case of metabolic liver disease, where the native liver is structurally normal and can drain bile, appropriate hepatocytes on scaffolds can be placed directly into the recipient liver. This intrahepatic engraftment would occur in relation to the normal host biliary system. The native liver would then be a chimera of patient cells and donor cells draining into the patient's biliary tree.

For this procedure to be successful, the function of the implanted cells, both in vitro as well as in vivo, must be determined. In vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with β-glucuronidase. Diconjugated and monoconjugated bilirubin can also be determined by thin layer chromatography after alkalinemethanolysis of conjugated bile pigments. In general, as greater numbers of functioning transplanted hepatocytes implant, the levels of conjugated bilirubin will increase. The same technique measuring monoconjugated and diconjugated bilirubin can be performed in vitro by testing the media for levels of these bilirubin conjugates. Analogous organ function studies can be conducted using techniques known to those skilled in the art, as required to determine the extent of cell function both in cell culture and after implantation.

Figure 4:
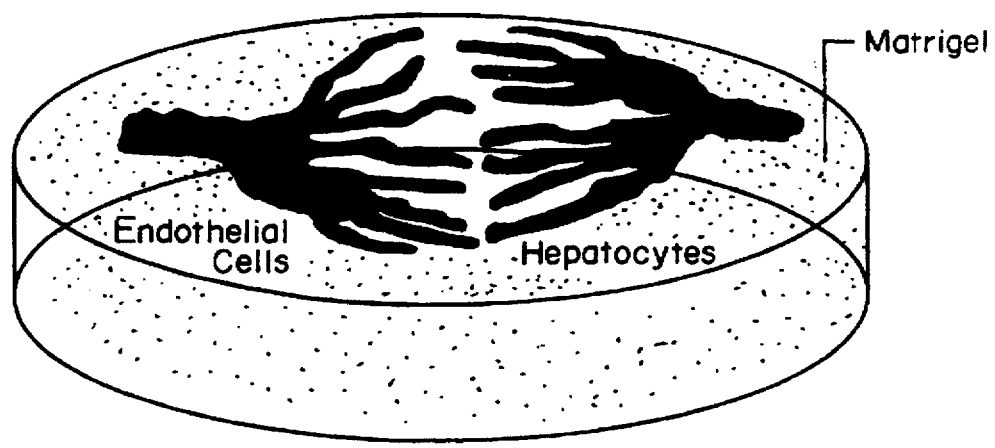
FIG. 4 is a diagram of a technique to study in vitro morphogenesis using biodegradable polymers, cells, and matrix.

In order to optimize conditions for forming implants, once in vitro and in vivo function has been confirmed, studies into morphogenesis of the structures can be initiated. Bile duct epithelial cells which have been harvested can be seeded onto polymer scaffolds. These scaffolds can then be reseeded with hepatocytes. The cell—cell interactions, shown schematically in FIG. 4, can be monitored in vitro by time lapse video microscopy as well as histological sections for light microscopy, transmission microscopy, and scanning electron microscopy.

Studies using labelled glucose as well as studies using protein assays can be performed to quantitate cell mass on the polymer scaffolds. These studies of cell mass can then be correlated with cell functional studies to determine what the appropriate cell mass is.

The following examples demonstrate actual attachment of cell preparations to bioerodable artificial polymers in cell culture and implantion this polymer-cell scaffold into animals. Using standard techniques of cell harvest, single cells and clusters of fetal and adult rat and mouse hepatocytes, pancreatic islet cells, and small intestinal cells have been seeded onto biodegradable polymers of polyglactin 910, polyanhydrides, and polyorthoester. Sixty-five fetuses and 14 adult animals served as donors. One hundred and fifteen polymer scaffolds were implanted into 70 recipient animals: 66 seeded with hepatocytes; 23 with intestinal cells and clusters; and 26 with pancreatic islet preparations. The cells remained viable in culture, and in the case of fetal intestine and fetal hepatocytes, appeared to proliferate while on the polymer. After 4 days in culture, the cell-polymer scaffolds were implanted into host animals, either in the omentum, the interscapular fat pad, or the mesentery. In 3 cases of fetal intestinal implantation coupled with partial hepatectomy, successful engraftment occurred in the omentum, one forming a visible 6.0 mm. cyst. Three cases of hepatocyte implantation, one using adult cells and two using fetal cells, have also engrafted, showing viability of hepatocytes, mitotic figures, and vascularization of the cell mass.

MATERIALS AND METHODS

Polymers:

Three synthetic absorbable polymers were used to fabricate filaments and discs as matrices for cell attachment, growth, and implantation (FIG. 2).

1. Polyglactin. This polymer, developed as absorbable synthetic suture material, a 90:10 copolymer of glycolide and lactide, is manufactured as Vicryl® braided absorbable suture (Ethicon Co., Somerville, N.J.) (Craig P. H., Williams J. A., Davis K. W., et al.: A Biological Comparison of Polyglactin 910 and Polyglycolic Acid Synthetic Absorbable Sutures. *Surg.* 141; 1010, (1975)).

2. Polyorthoesters. The specific polymer used was: 3,9-bis(ethylidene-2, 4, 8, 10-tetraoxaspiro[5.5] undecane copolymer with tran-1,4-cyclohexanedimethanol and 1,6-hexandiol in a molar ratio 2:1:1, respectively (SRI, California) (Heller J., Penhale W. H., Helwing R. F., et al.: Release of Norethindrone from Polacetals and Polyorthoesters. AIChE Symposium Series, 206; 77, pp. 28–36 (1981)).

3. Polyanhydride. The specific polymer used was a copolyanhydride of bis(1,4-carboxyphenoxy)propane and sebacic acid. It is biocompatible and has been used extensively in drug delivery applications (Heller J., Penhale W. H., Helwing R. F., et al.: Release of Norethindrone from Polyacetals and Polyorthoesters. AIChE Symposium Series, 206; 77, pp. 28–36 1981; Leong K. W., D'Amore P., Marletta M., et al: Bioerodable Polyanhydrides as Drug Carrier Matrices. II. Biocompatibility and Chemical Reactivity. *J. Biomed. Mat. Res.* 20: 51, 1986; Domb A. J., Langer R.: Polyanhydrides I. Preparation of High Molecular Weight Polyanhydrides. *J. Poly. Sci.*, in press; Kopacek J., Ulbrich K.: Biodegradation of Biomedical Polymers. *Prog. Poly. Sci* 9:1, (1983, and references within).

Polymer Configuration:

The polyglycolide was used as supplied by the manufacturer. Small wafer discs or filaments of polyanhydrides and polyorthoesters were fabricated using one of-the following methods:

A. Solvent Casting. A solution of 10% polymer in methylene chloride was cast on a branching pattern relief structure as a disc 10 mm in diameter for 10 minutes at 25° C. using a Carver press. After solvent evaporation, a film 0.5 mm in thickness with an engraved branching pattern on its surface was obtained.

B. Compression Molding. 100 mg of the polymer was pressed (30,000 psi) into a disc having a branching pattern relief, 10 mm in diameter and 0.5 mm thick.

C. Filament Drawing. Filaments were drawn from the molten polymer (30 microns in diameter). Small flattened 1.0 cm. tufts were used for the experiments.

D. Polyglactin 910. Multiple fibers of 90:10 copolymer of glycolide and lactide converging to a common base were fashioned from suture material of Q-Vicryl® by fraying the braided end of the polymer. These branching fiber clusters were approximately 1.0 cm. in height. The individual fibrils were 30 microns in diameter.

Animals:

Young adult and fetal Sprague-Dawley rats and C57 B1/6 mice (Charles River Labs, Wilmington, Mass.) were used as cell donors for all experiments. The animals were housed individually, allowed access to food and water ad lib, and maintained at 12 hour light and dark intervals. Animals were anesthetised with an IP injection of pentobarbital (Abbott Labs, North Chicago, Ill.) at a dose of 0.05 mg/g and supplemented with methoxyflurane (Pitman-Moore, Inc., Washington Crossing, N.J.) by cone administration. Fetal animals were harvested at 13, 17 and 20 days gestation for use as liver, pancreas, and intestinal donors. Young adult animals were used as liver and pancreas donors and as recipients of the cell-scaffold matrices.

Cell Harvest and Cell Culture

Liver:

After the induction of anesthesia, the abdomen of young adult animals was shaved, prepped with betadine, and opened using sterile technique. The liver was isolated and after heparinization with 100 U. of heparin (Elkins-Sinn, Inc., Cherry Hill, N.J.), the portal vein was cannulated with a 23 gauge plastic IV cannula (Critikon, Inc., Tampa, Fla.). The inferior vena cava was transected, the liver flushed with 2–3 cc.'s of sterile saline, removed from its bed, and transferred to a sterile dish where it was perfused with an oxygenated solution of 0.025% collagenase type II (BCA/ Cappel Products, West Chester, Pa.) by a technique modified from Selgen (Selgen, P. O.: Preparation of Rat Liver Cells, III. Enzymatic Requirements of Tissue Dispersion. *Exp. Cell. Res.* 82: 391, 1973). After a 20 minute perfusion, the liver was transferred to a sterile hood for cell dispersion and culture.

A two-step collagenase perfusion technique was utilized for hepatocyte harvest. The in vivo liver perfusion must involve a continuous flow of perfusate of 30–40 mm$^3$ per minute, rather than pulsatile perfusion. Initial hepatocyte harvests yielding 2–3×106 cells with a 10–20% cell viability were improved to yield a 4–6×108 cell harvest with a cell viability of 80–90% by switching to a peristaltic pump which provides a continuous flow. Various buffers have also been tested for their effect. For example, HEPES' buffer was used to decrease the acidity of the perfusate.

To avoid contamination of the hepatocyte polymer scaffolds in culture with either fungus or bacteria, sterile technique was used both for isolation and perfusion of hepatocytes. Antibiotics were also added to the collagenase perfusion solution.

Fetal animals were harvested by isolating and removing the gravid uterine horns from pregnant animals of the appropriate gestation. The intact uterus with multiple fetuses was transferred in saline to a sterile room, equipped with a dissection microscope. Individual fetuses were opened and the liver, intestine, and pancreas were harvested and pooled. Organs were then transferred to a sterile hood for cell isolation. The tissues were minced, treated with a 0.025% Type II collagenase, and dispersed into cell suspensions.
Pancreas:

After the induction of anesthesia, the abdomen of young adult animals was shaved, prepped with betadine, and opened in the midline using sterile technique. The common bile duct was isolated, and the pancreas visualized. 2.5 cc.'s of 2.0% Type II collagenase (BCA/Cappel Products, West Chester, Pa.), was infused into the pancreas by injection into the common bile duct using the technique described by Gotoh et al. (Gotoh M., Maki T., Kiyozumi T., et al.: An Improved Method of Isolation of Mouse Pancreatic Islets. Trans. 40; 4, pp. 436–438, 1985). After 5 minutes, the pancreas was transferred to a sterile hood for islet cell isolation. Briefly, the tissue was placed into a 25% Ficoll solution and layered under a discontinuous Ficoll gradient (23, 21, 11%) and centrifuged at 800×g. for 10 minutes. Islets which aggregated at the 21–11% interface were washed with cold Hank's solution and centrifuged at 320×g. 3 times. The islets were resuspended in RPMI 1640 (Gibco, Grand Island, N.Y.) media supplemented with 10% fetal calf serum, and overlaid onto polymer scaffolds. Fetal animals were harvested as donors as described above.
Intestine:

Fetal intestine was obtained as described above.
Polymer-Cell Scaffolds and Implantation:

Cells in suspension were plated onto polymer matrices at 1×10$^5$ or 1×10$^6$ cells/cc. They were maintained in Chee's media supplemented with 10% fetal calf serum for 3–4 days in a 10% CO2 environment. Viability of cells on the scaffold immediately pre-implantation was assessed by the trypan blue exclusion method. Young adult Sprague-Dawley rats were anesthetized, shaved over the operative site and prepped with betadine.

The polymer-cell scaffold was implanted in one of three sites:

1) the interscapular fat pad;

2) the omentum; and 3 the bowel mesentery.

Most animals underwent a partial hepatectomy to stimulate cell growth. Animals were sacrificed at day 3, 7, or 14 and the implants were examined histologically with hematoxylin and eosin. Polymers without cells served as controls. Polymer-cell scaffolds were examined histologically after 4 days in culture and before implantation to assess cell attachment and viability.

The following techniques are also used in the examination of the cell-matrix structures.

Immunofluorescent staining: tissue, including the cell-polymer scaffold, is frozen by immersion into isopenthane liquid, stored at −70° C. in a cryostat and mounted on albumin-coated slides. After thawing for 15–30 minutes at room temperature, the slides are washed with phosphate-buffered saline (PBS). Several drops of appropriately diluted, commercially prepared fluorescine isothyocyanate (FITC) antisera labelled to the appropriate monoclonal antibody, for example, the HY antigen or other markers of hepatocyte membranes, are applied individually to separate moist biopsy sections. They are incubated at room temperature for 30 minutes in a moist chamber. Following rinses with PBS the sections are cover-slipped with a glyceral-PBS mixture and examined using an immunofluorescence microscope (Leitz) with epi-illumination and a high pressure mercury lamp as the light source.

Electron microscopy: samples for electron microscopy are obtained from fresh tissue and fixed in 2% glutaraldehyde, post-fixed in 1% osmiumtetroxide, dehydrated in graded alcohols, and imbedded in epon-8:12. One micron thick section of the plastic imbedded tissue are made from areas of interest. Selected blocks are trimmed, ultrathin sections made, and stained with uranyl acetate and lead citrate, and examined with a Phillips 300× electron microscope. Scanning electron microscopy (SEM): After hepatocytes are isolated and attached to the appropriate polymer, they are incubated for the appropriate interval. After culture, samples are prepared for SEM by incubating in a 50:50 solution of 2% glutaraldehyde phosphate buffer solution for 1 hour, the samples are then rinsed 4 times in PBS for 10 minutes per rinse to remove excess glutaraldehyde solution. Samples are dehydrated using progressively increasing ethanol solutions. Samples are then placed in a critical point dryer where ethanol is exchanged for liquid $CO_2$. Temperature is gradually increased to the critical point, ensuring dehydration. The samples are then coated with a thin layer of gold and placed under high vacuum in the scanning electron microscope.

Seventy-nine animals which included 14 adults and 65 fetuses were used as donors for cell harvest; 115 polymer scaffolds were prepared for implantation. Sixty-six of these scaffolds were seeded with hepatocytes, 23 with intestinal cells and clusters, and 26 with pancreatic islets and cell preparations. Implantation was performed in 70 recipient animals. Fifty-eight were sacrificed at 7 days for histologic examination of the implant while 3 were examined at 3 days, and 9 at 14 days after implantation.

Figure 5:
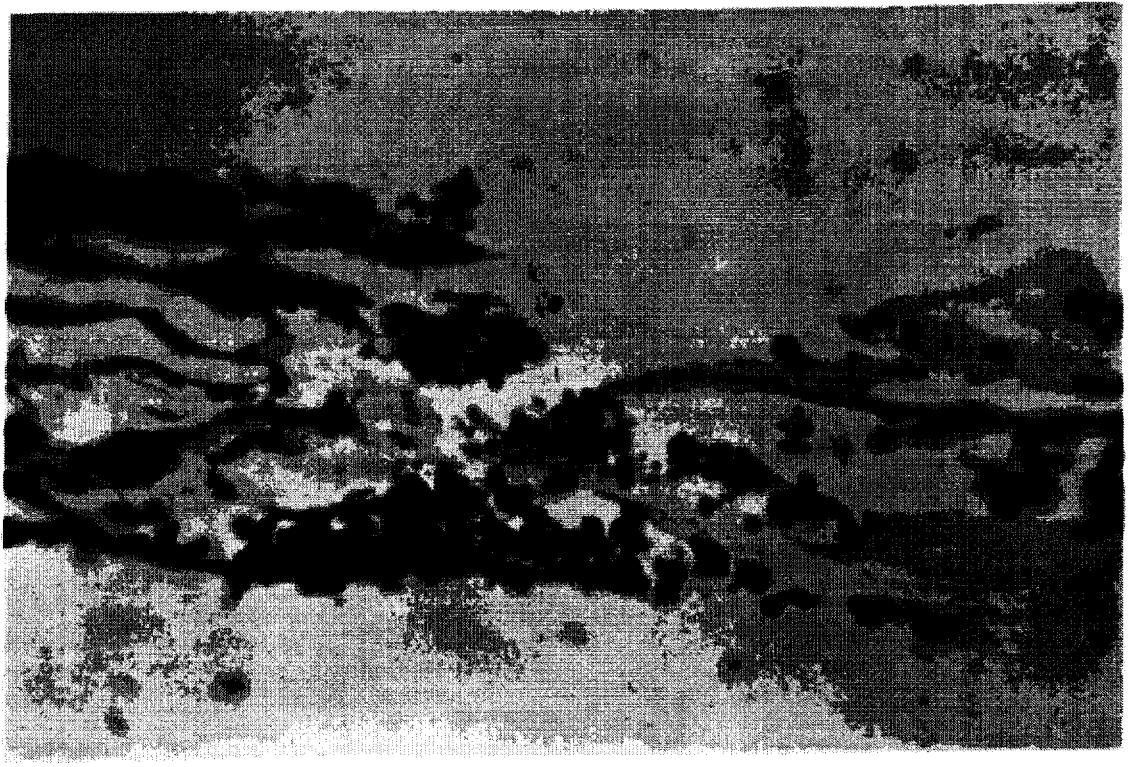
FIG. 5 is a photograph (172×) of hepatocytes attached to fibers of polyglactin 910 after 4 days in culture. Cells are stained with Hematoxylin and Eosin.
Figure 6:
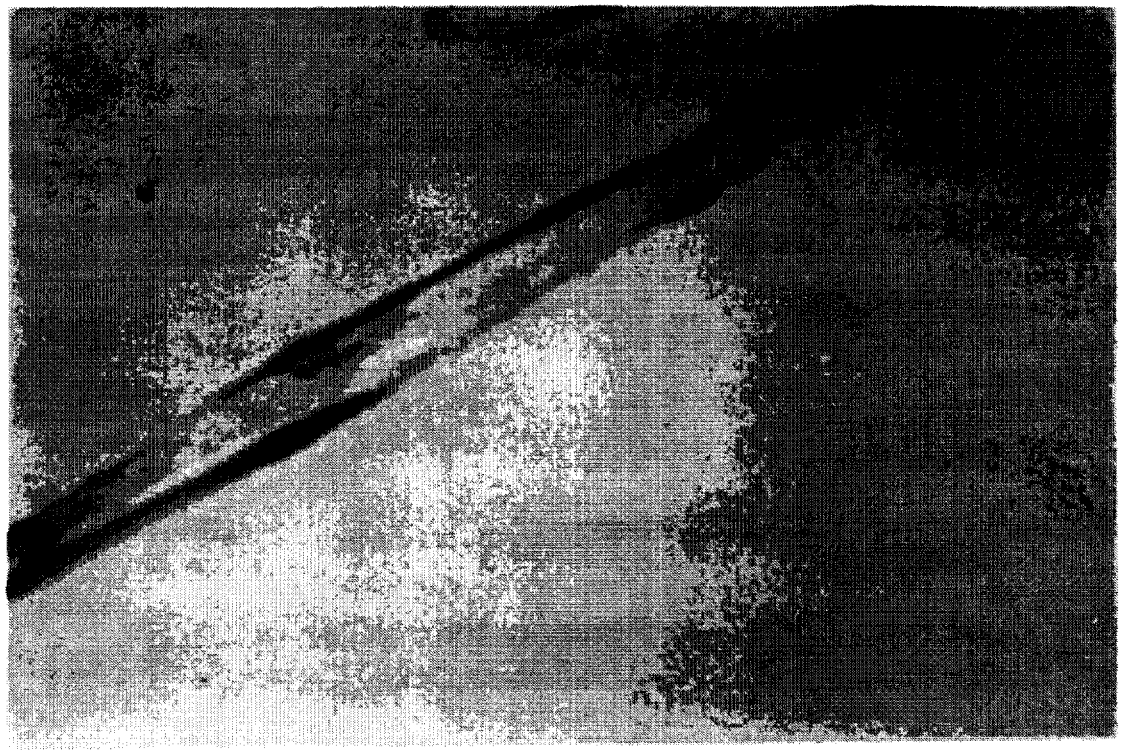
FIG. 6 is a photograph of bile duct epithelial cells cultured on polymer fibers for one month.
Figure 8:
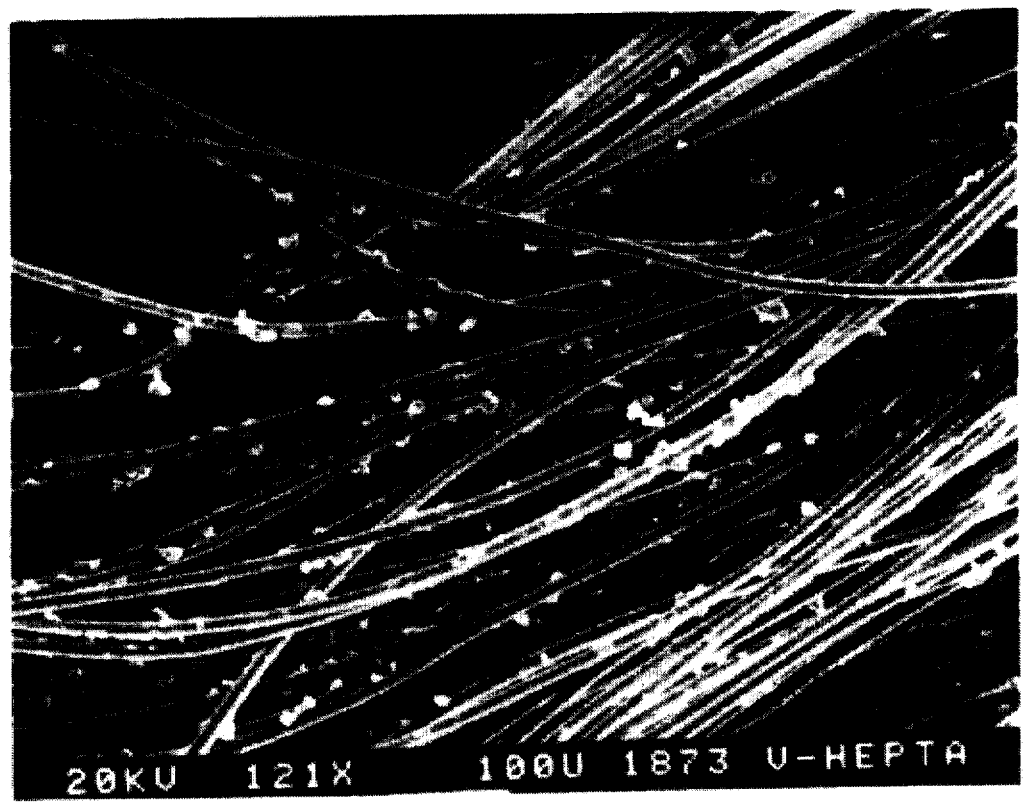
FIG. 8 is a scanning electron micrograph (121×) of hepatocytes attached to polymer fibers for one week.
Figure 9:
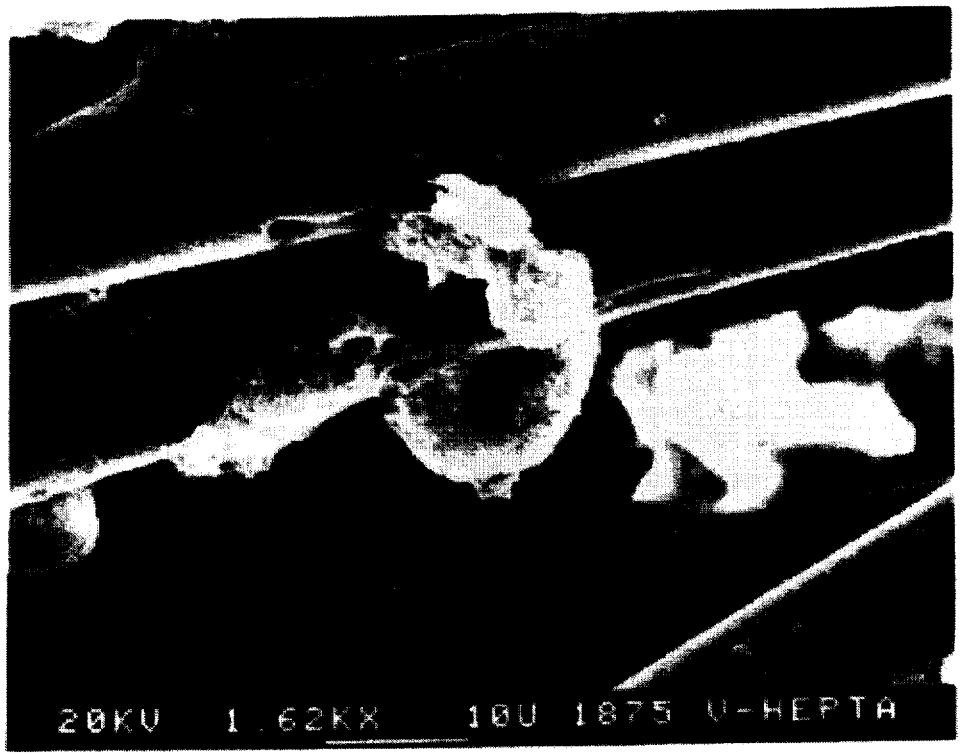
FIG. 9 is a higher magnification (1600×) of the hepatocytes on polymer fibers of FIG. 8.

Cell viability on the polymer scaffold at 3 to 4 days in culture varied with the type of polymer material used. FIG. 5 shows hepatocytes on polymer matrices for four days. FIG. 6 shows bile duct epithelial cells on polymer fibers for one month. FIGS. 8 and 9 show hepatocytes attached to polymer fibers for one week. Less than 10% of the cells were viable on the polyanhydride discs, whereas 80% of cells cultured on polyorthoester discs and filaments remained viable, and over 90% survived on polyglactin 910.

Hepatocytes placed on polygalactin fibers for three weeks in culture showed evidence of significant proliferation with nodule formation one to three mm in diameter with fragmented fibers interspersed within the cell mass.

Blood vessel ingrowth was noted three days after implantation with all of the polymer types and configurations. In the implanted fiber networks, new blood vessels formed in the interstices between the polymer filaments. The polymer discs showed capillary formation immediately adjacent to the polymer material. This angiogenic response accompanied an inflammatory infiltrate which displayed both an acute phase and a chronic foreign body reaction to the implanted polymers. The intensity of inflammation varied with the polymer type tested: polyanhydride elicited the most severe acute and chronic response although the inflammation surrounding branching fibers of either polyorthoester or polyglactin appeared proportionately greater than the disc configuration because of the greater surface area of exposed foreign material to host.

Figure 7:
FIG. 7 is a photograph (172×) of an implant of hepatocytes from an adult rat donor into omentum. The polymer-cell implant has been in place for 7 days before sacrifice. Hepatocytes are healthy and several mitotic figures can be seen. Blood vessels are present in the mass. To the left, an inflammatory infiltrate in the area of the polymer is observed. Cells are stained with Hematoxylin and Eosin.

Histologic examination of liver cell implants in 3 animals showed evidence of successful engraftment of hepatocytes at seven days, as shown by FIG. 7. Small clusters of healthy appearing hepatocytes were seen with bile canaliculi between adjacent cell membranes and some areas demonstrated mitotic figures. The cells were surrounded by an inflammatory response and blood vessels coursed around and through the cell clusters. Polymer material was seen immediately adjacent to the cells.

Figure 10:
FIG. 10 is a photomicrograph (10×) of an intestinal cell implant into omentum ten days after implantation. It shows a 6 mm cystic structure that has formed in the omentum with blood vessels streaming into it. Polymer fibers can be seen in the wall of the cyst.
Figure 11:
FIG. 11 is a photograph (172×) of a cross-section of the cyst of FIG. 10 demonstrating a luminal structure lined by intestinal epithelial cells. These cells show polarity. The lumen contains cellular debris and mucous. The white oval areas to the left of the lumen represent polymer fibers. They are surrounded by an inflammatory infiltrate and new blood vessels. A layer of smooth muscle can be seen to the right of the lumen, suggesting that this cyst may have arisen from a small intestinal fragment. Hematoxylin and Eosin.

Successful engraftment of intestinal cells and clusters were observed in 3 animals. Histologic findings were similar to the hepatocyte implants. On gross examination of the implant at 7 days, a cystic structure approximately 6.0 mm in length was found at the implant site with polymer fibers displayed within its wall (FIG. 10). Microscopic examination revealed well differentiated intestinal epithelium lining the cavity with mucous and cellular debris within the lumen, shown in FIG. 11. One wall of the cyst contained polymer fibers, blood vessels, and inflammatory cells immediately adjacent to the intestinal epithelium. The other wall included a muscular coating which suggested that the polymer held a small minced piece of fetal intestine as the origin of the cyst which eventually developed. The cyst displayed well differentiated intestinal epithelium with mucous secreting cells. Other clusters of intestinal epithelium demonstrated active mitosis.

Control polymers implanted without prior cell seeding elicited an angiogenic and inflammatory response similar to their counterparts which had been seeded with parenchymal cells and maintained in culture. This suggested that the cells themselves did not play a major role in the inflammation and neovascularization seen. If appropriate, immunosuppressant drugs may be injected or incorporated into the polymer structure. However, a limited inflammatory reaction to the implant may in fact be desirable to promote growth. This encourages a more normal healing response and may play a role in the "calling in" of new blood vessels.

The use of the donor's own cells or cells from which the lymphocytes have been removed prior to culturing is especially important in the culturing and implantation of intestinal cells. If the lymphocytes are not removed from the intestinal cells prior to implantation, the result can be "graft vs. host" disease. The present invention decreases this possibility since only the cells needed for function are placed on the polymers and implanted into the patient.

Figure 12:
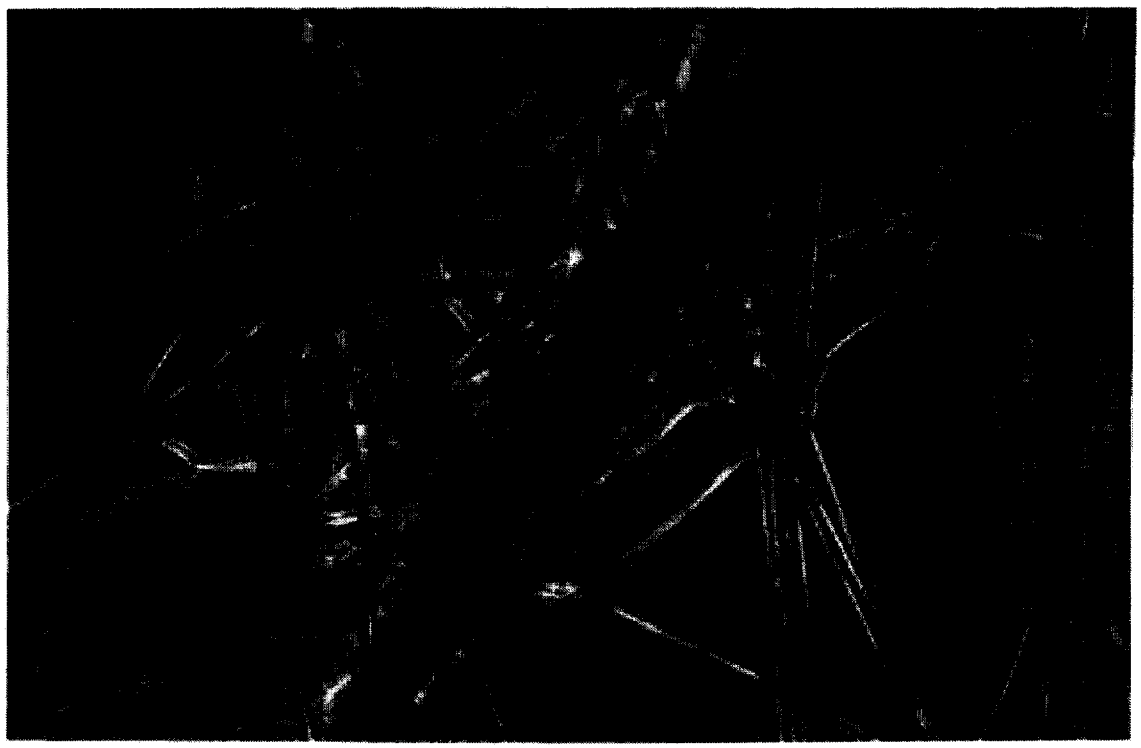
FIG. 12 is a photograph of Islets of the pancreas attached to polymer fibers after four weeks in culture, showing some secretion of insulin in response to glucose.
Figure 13:
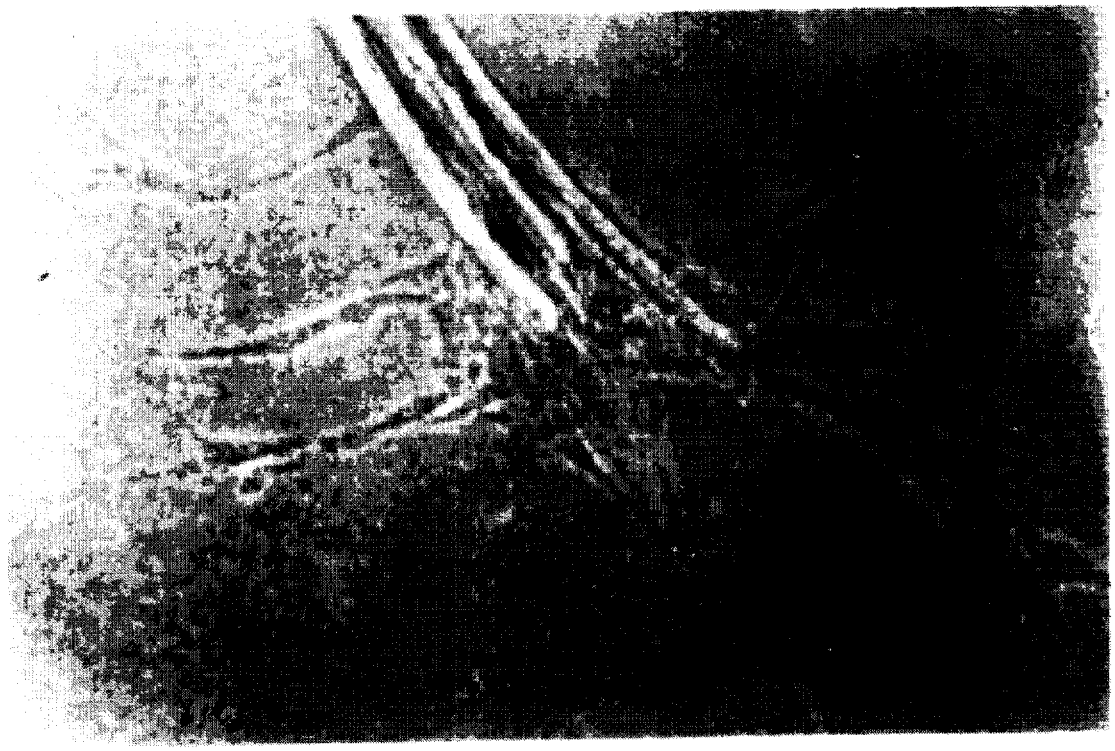
FIG. 13 is a photograph of polymer fibers seeded with bovine aortic endothelial cells in a biomatrix. The cells can be seen migrating off the polymer into the matrix in a branch-like orientation.
Figure 14:
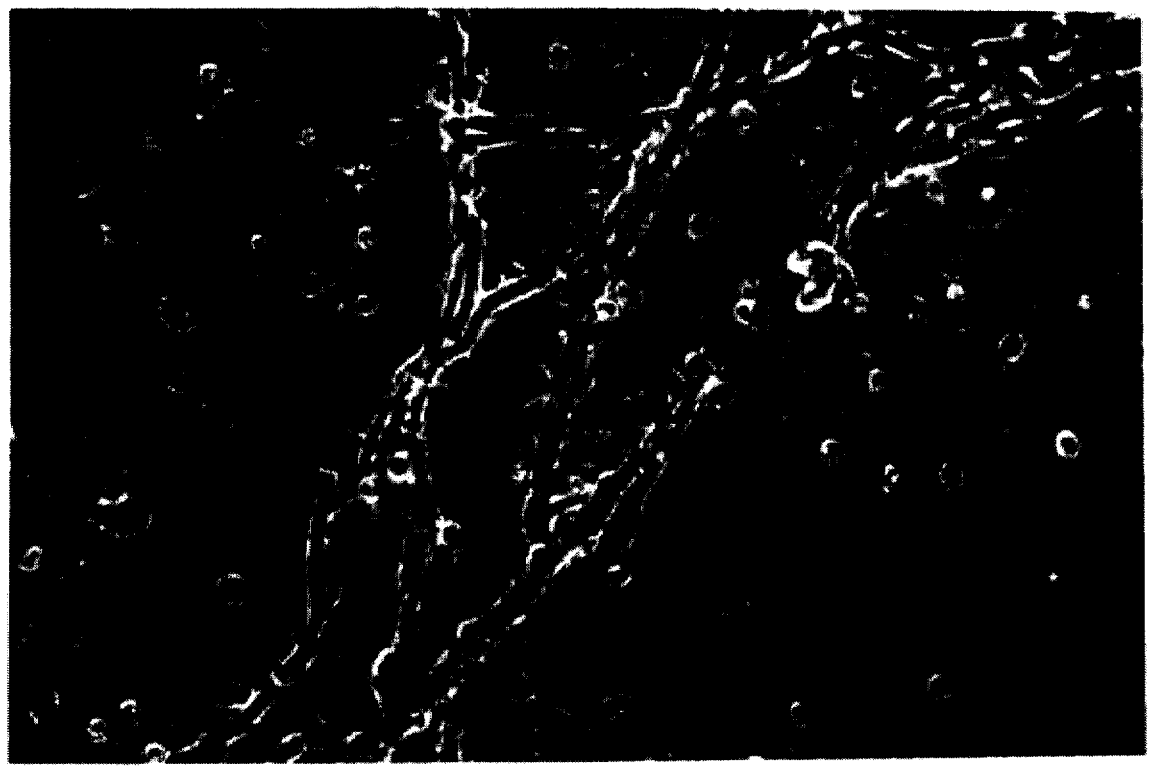
FIG. 14 is a photograph of bovine aortic endothelial cells attached to polymer fibers after one month in culture.

Other types of cells which have been successfully cultured and demonstrated to retain function include pancreatic cells and aortic cells. FIG. 12 is a photograph of Islets of the pancreas attached to polymer fibers after four weeks in culture, showing some secretion of insulin in response to glucose. FIG. 13 is a photograph of polymer fibers seeded with bovine aortic endothelial cells in a biomatrix. The cells can be seen migrating off the polymer into the matrix in a branch-like orientation. FIG. 14 is a photograph of bovine aortic endothelial cells attached to polymer fibers after one month in culture. These cells have been shown to reform structure. Their ability to do so depends upon the environment in which they are placed and the degree of alteration they have undergone. In addition to the the bile duct cells which formed tubules in vitro) as shown in FIG. 6, the aortic endothelial cells attached to polymer fibers formed branching tubule structures after one month in culture. As the polymer fibers resorbed, the cells maintained their orientation, indicating that they secreted their own matrix to maintain their geometric configuration.

Figure 15:
FIG. 15 is a phase contrast photomicrogarph showing polymer fibers coated with mouse fetal fibroblasts. The fibroblasts can be seen streaming off the polymer fibers in a straight line onto the culture dish.

FIG. 15 is a phase contrast photomicrogrph showing polymer fibers coated with mouse fetal fibroblasts. The fibroblasts can be seen streaming off the polymer fibers in a straight line onto the culture dish. This indicates that cell—cell orientation cues have been maintained as they migrate off the polymer fiber.

Figure 16:
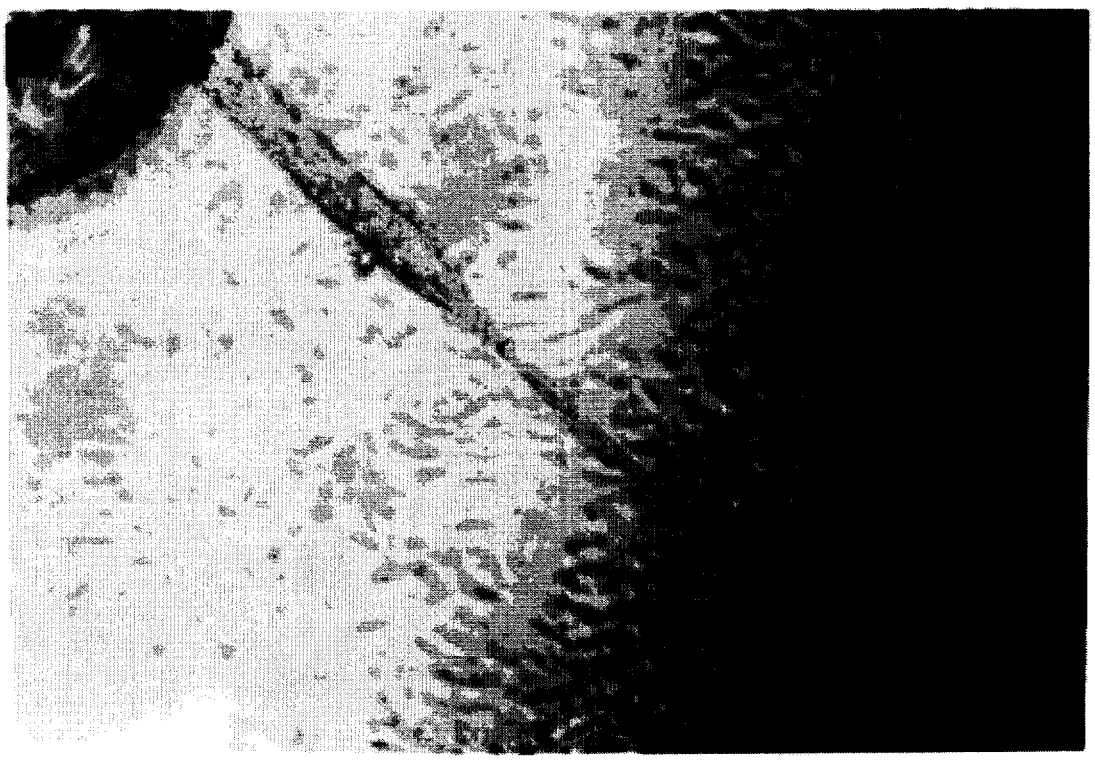
FIG. 16 is a phase contrast photomicrograph of polymer fibers coated with mouse fetal fibroblasts. These fetal fibroblasts have migrated off of the polymer through media and have attached at the bottom of the tissue culture plate.

FIG. 16 is a phase contrast photomicrograph of polymer fibers coated with mouse fetal fibroblasts. These fetal fibroblasts have migrated off of the polymer through media and have attached at the bottom of the tissue culture plate. This shows that a living tissue bridge has been created between the polymer fiber and the tissue culture bottom by fetal fibroblasts, indicating their spatial organization.

These studies demonstrate that cells of liver, intestine, and pancreas will successfully attach and remain viable on polymers in cell culture and that liver and intestinal cells will successfully engraft in a host animal. The following methods were used to demonstrate the optimization of cell attachment to polymers, using liver and pancreas as model systems.

A nonquantitative cell attachment study was undertaken in which N.I.H. 3T3 cells were used as model cells for attachment studies. Polymers tested included polyglactin, polyorthoester, and polyanhydride. Attachment studies were then performed on pancreatic islets.

POLYMER PREPERATION

Polyglactin 910, polyorthoester, and polyanhydrides were treated with several different buffers in an effort to change the surface conformation of the polymer, and were coated with various materials thought to be important for cell attachment. Each polymer was tested by soaking in a citric acid buffer solution, pH 4.0, phosphate buffer solution, pH 7.0, or a carbonate buffer, pH 10.0. These were incubated at 37° C. for 2, 5, or 7 days. Surface characteristics of the polymer material were characterized by scanning electron microscopy (SEM) at magnifications of 500× and 1700×.

Different coatings included: agar at 2% and 5% solutions, agarose at 2%, 6%, and 7% solutions, gelatin at 1.5% and 11% and gum arabic at 1.5% and 11%. Coatings were prepared by making a solution of the appropriate weight of material in deionized water and autoclaving for 30 minutes. Solutions were maintained in the liquid state in a warm water bath at 40°–50° C. until used. Using sterile technique, each polymer was immersed into the appropriate coating material. Gelatin was cross-linked with a 50:50 solution of 2% gluteraldehyde:phosphate buffer for 1 hour. A combined coating using gelatin and gum arabic was tested. Collagen coated polymers were prepared by covering the polymer with a Type IV collagen and lyophilizing this polymer-collagen material overnight. Some collagen coated samples were immersed in phosphate buffer for one hour. All samples were examined by SEM to determine uniformity of coating. All samples were sterilized using UV exposure under the sterile hood for 8–12 hours. Cells were then added for cell attachment studies.

Cell Attachment Studies.

Cell polymer samples were examined by phase contrast microscopy and SEM using the following sample preparation technique. Samples were fixed by immersion in 50:50 2% gluteraldehyde:phosphate buffer for 1 hour and then rinsed ×3 for 20 minutes with phosphate buffer. They were then dehydrated in progressively increasing concentrations of ethanol solutions (70%, 80%, 90%, 95%) for 20 minutes each, immersed in absolute alcohol overnight, dried by critical point drying with liquid $CO_2$ and coated with gold.

Isolation and purification of Pancreatic Islet Cells

Young adult mice were anesthetized and underwent a midline abdominal incision using sterile technique. The common bile duct was isolated and cannulated with a 30 gauge needle. 2.5 cc. of Type IV collagenase was slowly infused through the common bile duct with a clamp on the duodenum so that there would be retrograde flow into the pancreatic duct. The pancreas was then removed and digested with collagenase for 45 minutes at 37° C. The pancreas was then washed with cold Hank's solution and pancreatic tissue passed through a nylon mesh filter. The islets were then isolated using a discontinuous Ficoll gradient, then washed with cold Hank's solution and resuspended in RPMI 1640 media enriched with 10% fetal calf serum. Islets were placed in 24 well plates on the appropriate polymer and incubated at 37°, 10% CO2.

N.I.H. 3T3 cells were used as a cell line for other attachment studies.

Figure 17:
FIG. 17 is a scanning electron micrograph (472×) of a polyanhydride fiber immersed in a phosphate buffer solution, indicating that immersion of polymer fibers in differing buffers can alter the polymer surface and, therefore, influence cell attachment and differentiation.

FIG. 17 is a scanning electron micrograph (472×) of a polyanhydride fiber immersed in a phosphate buffer solution, indicating that immersion of polymer fibers in differing buffers can alter the polymer surface and, therefore, influence cell attachment and differentiation.

Figure 18:
FIG. 18 is a scanning electron micrograph (493×) of polymer fibers coated with 1% gelatin, showing that the polymer fibers can be coated with cell adhesion agents to increase cell attachment.

FIG. 18 is a scanning electron micrograph (493×) of polymer fibers coated with 1% gelatin, showing that the polymer fibers can be coated with known cell adhesion agents to increase cell attachment.

Table I is the attachment of 3T3 cells on Vicryl™ after 5 days in culture. Maximum attachment was found with polymer coated with 11% gelatin, collagen, and collagen in phosphate buffer. Table II is the attachment of 3T3 cells on polyorthoester, after 2 days and after 5 days. After 2 days there was maximum attachment on polymer coated with crosslinked 11% gelatin-11% gum. After 5 days, there was maximum attachment on polymer coated with crosslinked 11% gelatin. PH was demonstrated to affect cell attachment: maximum attachment occurred at pH 7 for 5 days and pH 10 for 2 days. Table III demonstrates 3T3 cell attachment on polyanhydride. Maximum attachment occurred with uncoated polyanhydride after 2 days. Materials other than those listed were not studied due to polymer degradation. Table IV described the attachment of pancreatic cells (islets and fibroblasts)on vicryl™ after two weeks in culture. Maximum attachment occurs with polymer coated with crosslinked or uncrosslinked 11% or 1.5% gelatin and collagen. Very little attachment of these cells to polyorthoester and polyanhydride samples was observed. Table V is the attachment of islet cells after two weeks in culture, with maximum attachment again occurring with polymer coated with collagen.

TABLE I

3T3 CELLS ON VICRYL[R] AFTER 5 DAYS IN CULTURE

| Polymer | Attachment |
| --- | --- |
| Control (untreated Vicryl[R] with no cells) | Very little degradation |
| Untreated | 0 |
| Agar (5%) | 1 |
| Agarose (6.7%) | 1 |
| Gelatin (11%) - crosslinked | 2 |
| Gelatin (11%) | 4 |
| Gelatin (1.5%) - crosslinked | 3 |
| Gum arabic (11%) | 1 |
| Gelatin (11%) Gum arabic (11%) - crosslinked | 2 |
| Collagen | 4 |
| Collagen - phosphate | 4 |
| pH 4, 2 days | 1 |
| pH 4, 5 days | 0 |
| pH 4, 7 days | 0 |
| pH 7, 2 days | 3 |
| pH 7, 5 days | 2 |
| pH 7, 7 days | 1 |
| pH 10, 2 days | 0–1 |
| pH 10, 5 days | 0 |
| pH 10, 7 days | 0 |

Scale
0 No viable cells
1 Minimal cell attachment
2 Moderate cell attachment
3 Good cell attachment
4 Better cell attachment
5 Excellent cell attachment

TABLE II

3T3 CELLS ON POLYORTHOESTER

| Polymer | Attachment after 2 days | Attachment after 5 days |
| --- | --- | --- |
| Control (untreated, with no cells) | Some degradation | Considerable degradation |
| Untreated | 1 | 1 |
| Agar (5%) | 1 | 1 |
| Agarose (6.7%) | 1 | 1 |
| Gelatin (11%) crosslinked | 2 | 4+ |
| Gelatin (11%) gum 11% crosslinked | 4 | 2 |
| Gum arabic (11%) | 1 | 1 |
| pH 4, 2 days | 1 | 0 |
| pH 4, 5 days | 2 | 1 |
| pH 4, 7 days | 1 | 1 |
| pH 7, 2 days | 3 | 2 |
| pH 7, 5 days | 4 | 3 |
| pH 7, 7 days | 2 | 1 |
| pH 10, 2 days | 4+ | 4+ |
| pH 10, 5 days | 0 | 0 |
| pH 10, 7 days | 4 | 3 |

Scale
0 No viable cells
1 Minimal cell attachment
2 Moderate cell attachment
3 Good cell attachment
4 Better cell attachment
5 Excellent cell attachment

TABLE III

3T3 ON POLYANHYDRIDE

| Polymer Control (untreated, no cells) | Attachment after 2 days | Attachment after 5 days |
| --- | --- | --- |
| Untreated | 4+ | 2 |
| Agar (5%) | 0 | 0 |
| Agarose (6.7%) | 0 | 0 |
| Gum arabic (11%) | 2 | 0 |

Scale
0 No viable cells
1 Minimal cell attachment
2 Moderate cell attachment
3 Good cell attachment
4 Better cell attachment
5 Excellent cell attachment

TABLE IV

PANCREATIC CELLS ON VICRYL[R] AFTER 2 WEEKS IN CULTURE (MIXTURE OF ISLETS AND FIBROBLASTS)

| Polymer | Attachment |
| --- | --- |
| Control (untreated, no cells) | Little, if any degradation |
| Untreated | 0 |
| Agar (2%) | 1 |
| Agarose (2%) | 1 |
| Gelatin (11%) crosslinked | 4 |
| Gelatin (11%) | 4+ |
| Gelatin (1.5%) crosslinked | 2 |
| Gelatin (1.5%) | 4+ |
| Gum arabic (1.5%) | 1 |
| Gelatin (1.5%)/Gum arabic (1.5%) crosslinked | 1 |
| Gelatin (1.5%)/Gum arabic (1.5%) | 2 |
| Collagen | 4++ |
| Collagen - phosphate buffer | 3 |
| pH 4, 2 days | 0 |
| pH 4, 4 days | 0 |
| pH 7, 2 days | 1 |
| pH 7, 4 days | 2 |
| pH 10, 2 days | 1 |

Scale
0 No viable cells
1 Minimal cell attachment
2 Moderate cell attachment
3 Good cell attachment
4 Better cell attachment
5 Excellent cell attachment

TABLE V

PANCREATIC ISLETS ON VICRYL[R] AFTER 2 WEEKS IN CULTURE

| Polymer | Attachment |
| --- | --- |
| Control (untreated, no cells) | Very little degradation |
| Untreated | 0 |
| Gelatin (11%) crosslinked | 2 |
| Gelatin (11%) | 4 |
| Gelatin (1.5%) | 3 |
| Collagen | 4++ |

TABLE V-continued

PANCREATIC ISLETS ON VICRYL[R] AFTER 2 WEEKS IN CULTURE

| Polymer | Attachment |
| --- | --- |
| pH 7, 5 days | 2 |
| pH 10, 3 days | 2 |

Scale
0 No viable cells
1 Minimal cell attachment
2 Moderate cell attachment
3 Good cell attachment
4 Better cell attachment
5 Excellent cell attachment The method of the present invention is highly versatile and useful both in vivo and in vitro. For example, cells on polymer fibers embedded in Matrigel can be used to create three-dimensional organ structures in vitro. For in vivo applications, the polymer structure is tailored to fit the cells so that the desired function and structure is obtained after implantation, and so that cell growth, proliferation and function can be achieved initially in cell culture. The criteria for successful growth and implantation is when the transplant demonstrates functional equivalency to the organ which it is replacing or supplementing. For example, a functional kidney would not necessarily have to manufacture renin as long as it functions as an effective dialysis apparatus, removing concentrated low molecular weight materials from the bloodstream. A functional liver may only need to produce protein such as coagulation factors and excrete bile. For this purpose the liver transplant could be implanted in the omentum, the fatty, highly vasculated membrane adjacent to the small intestine. A functional intestine should be able to absorb sufficient nutrients to sustain life. This could be in the form of caloric solutions rather than normal "foodstuffs". "Secretory" organs in addition to a liver or a pancreas can be made by applying the same method of selecting secretory cells, constructing a matrix, culturing the cell on the matrix, and implanting the cell-matrix structure into an area which promotes vascularization of the cell-matrix structure.

Figure 19:
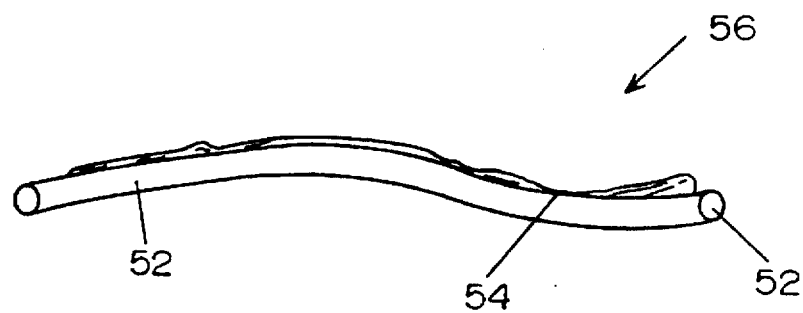
FIG. 19 is a perspective drawing of a bioabsorbable polymer fiber used for growth of nerve cells.

As demonstrated in FIG. 19, "organs" other than secretory organs can be made using the method of the present invention. Nerves may be constructed using long fibers 52 containing an appropriate nerve cell 54 to form a nerve structure 56. Following growth of the nerve along the length of the fiber, the structure 56 is implanted at the appropriate location extending from a nerve source to the area in which nerve function is desired.

Figure 20A:
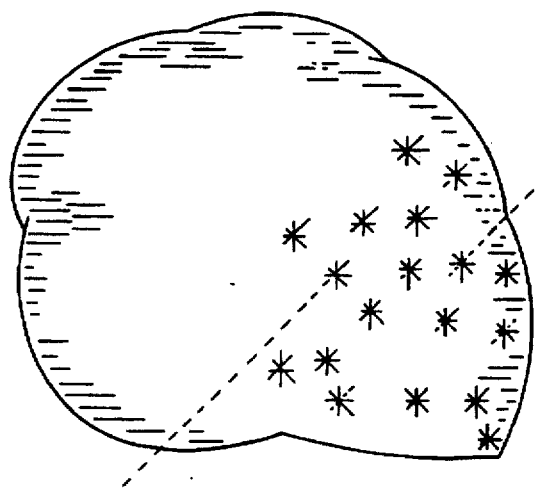
FIG. 20a is a plan drawing of polymer spicules seeded with heart muscle cells and implanted on the myocardium of the heart.
Figure 20B:
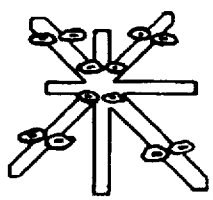

As shown in FIG. 20a and FIG. 20b, the present invention can be utilized in patients suffering from cardiac myopathy. Muscle cells are grown on polymer spicules (FIG. 20b), which are then embedded on the surface of the heart itself (FIG. 20a). In accordance with the previously discussed principles, the damaged heart itself would not be replaced but new, strong muscle tissue would grow across the damaged area, beating in synchrony with the underlying tissue, and restoring some of the lost function and partially remodeling the scar tissue.

A number of different methods have been used to create an artificial skin, primarily for use in treating burn patients. The most successful of these use a biodegradable matrix of collagen which is seeded with epithelial cells, attached to the wound site and overlaid with a moisture impermeable membrane formed of a non-degradable material such as silicone.

Although these methods are claimed to be useful in the construction of other organs having a smaller surface area and larger volume, such as liver and pancreas, they are not effective when actually attempted. There is no recognition of the need to provide a high surface area structure which allows attachment and proliferation of cells in vitro, prior to implantation. To be successful, the structure must be designed to allow adequate diffusion of nutrients, waste removal, and respiration in the absence of vascularization. Unless the cells are more or less equally exposed to the media, with as shallow of a concentration gradient as possible, this will not occur. As the cells multiply, the passage of nutrients, wastes, and gases to and from the cells becomes limited and the cells farthest from the media die. Since the artificial skin implants were immediately-placed on the underlying tissue so that capillary growth into the matrix begins prior to any significant increase in cell density, this has not previously been a consideration.

The concept of Chimeric Neomorphogenesis hinges upon the ability of cells to be nourished by diffusion until vascular ingrowth of the growing cell mass occurs. It was hypothesized that solid implants of a cell-matrix configuration using collagen or gelatin seeded with cells are limited in size by the physical constraints of diffusion. Others are presently using complex natural matrices seeded with cells to produce "organ equivalents". One is a collagen gel that appears to be a hydrated solution of Type I collagen. The following experiment tests the ability of this hydrated collagen to allow diffusion of nutrients to a cell population.

Figure 21A:
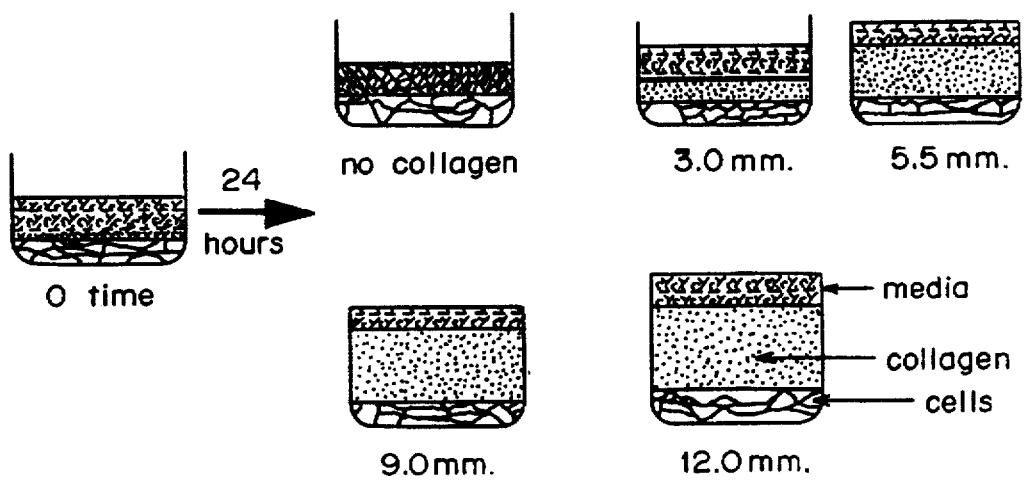
FIG. 21a is a cross sectional view of wells containing various thicknesses of collagen (0, 3.0 mm, 5.5 mm, 9.0 mm, and 12.0 mm) interspersed between bovine capillary endothelial cells and the media.

Bovine capillary endothelial cells were plated in gelatin coated 24 well tissue culture dishes and allowed to attach overnight. The initial cell number was $1 \times 10^5$ cells. The following day the cells were overlayed with different volumes of collagen Type I at a final solution of 0.32%. A standard volume of media was placed over the collagen so that the distances of nutrient source varied to the cells. The media was optimized for growth of bovine capillary endothelium. Dulbecco's minimal essential media, 10% calf serum, and retinal-derived growth factor at a concentration of 10 µl/ml were used. As depicted in FIG. 21a, the thickness of collagen interspersed between the cells and the media was 0, 3.0 mm, 5.5 mm, 9.0 mm, and 12.0 mm. At 24 hours, the media and collagen were removed and the cells were counted.

Figure 21B:
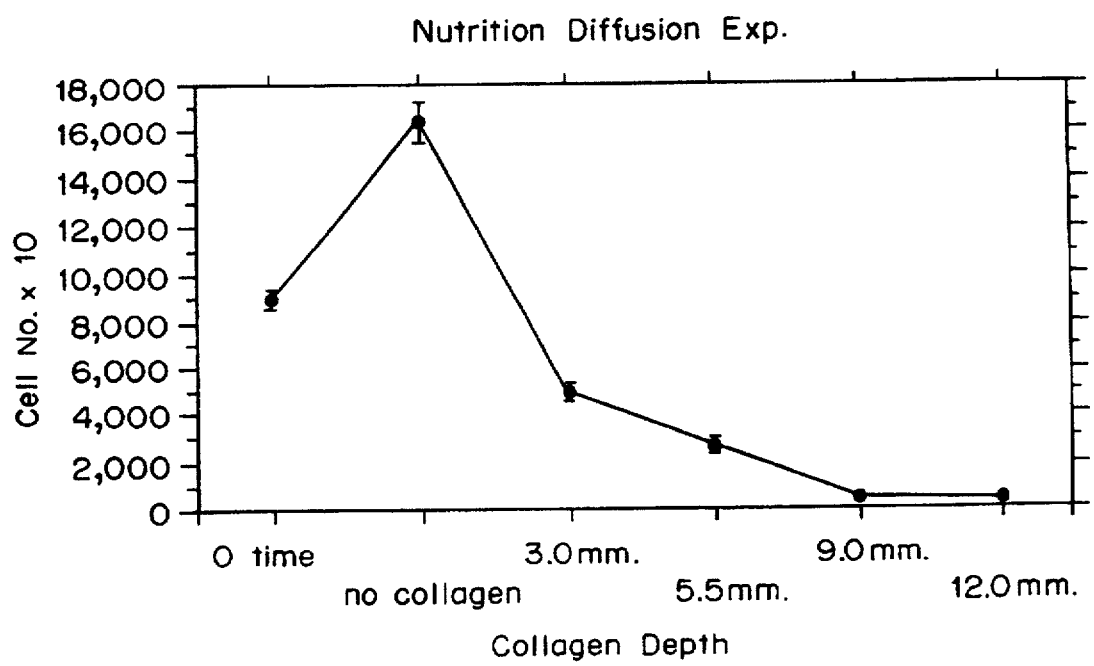

The experimental results, graphed in FIG. 21b, were essentially as predicted. As the thickness of the hydrated collagen matrix was increased, the cell viability decreased. Initial cell counts after cell attachments were 89,580±3719. Cells adjacent to media without the interposition of a collagen matrix doubled in a 24 hour period to 163,233±8582. A hydrated collagen gel of 3 mm in thickness between media and cells resulted in a cell number 49,587±3708. This decreased to 26,513±3015 at 5.5 mm, 4593±899 at 9 mm and 5390±488 at 12 mm. All of the cells at 9 and 12 mm were rounded and nonviable.

Figure 22A:
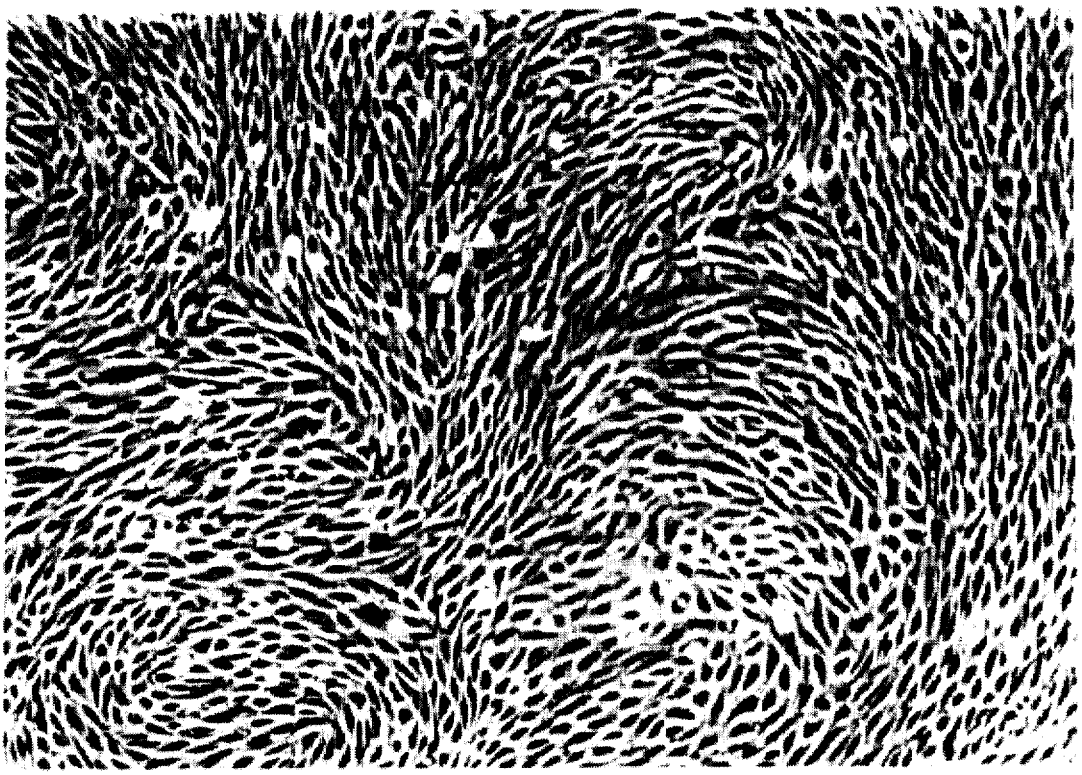
FIGS. 22a–c are photographs demonstrating the effect of diffusion distance on cell viability and proliferation diagrammed in FIGS. 21a and 21b.
Figure 22B:
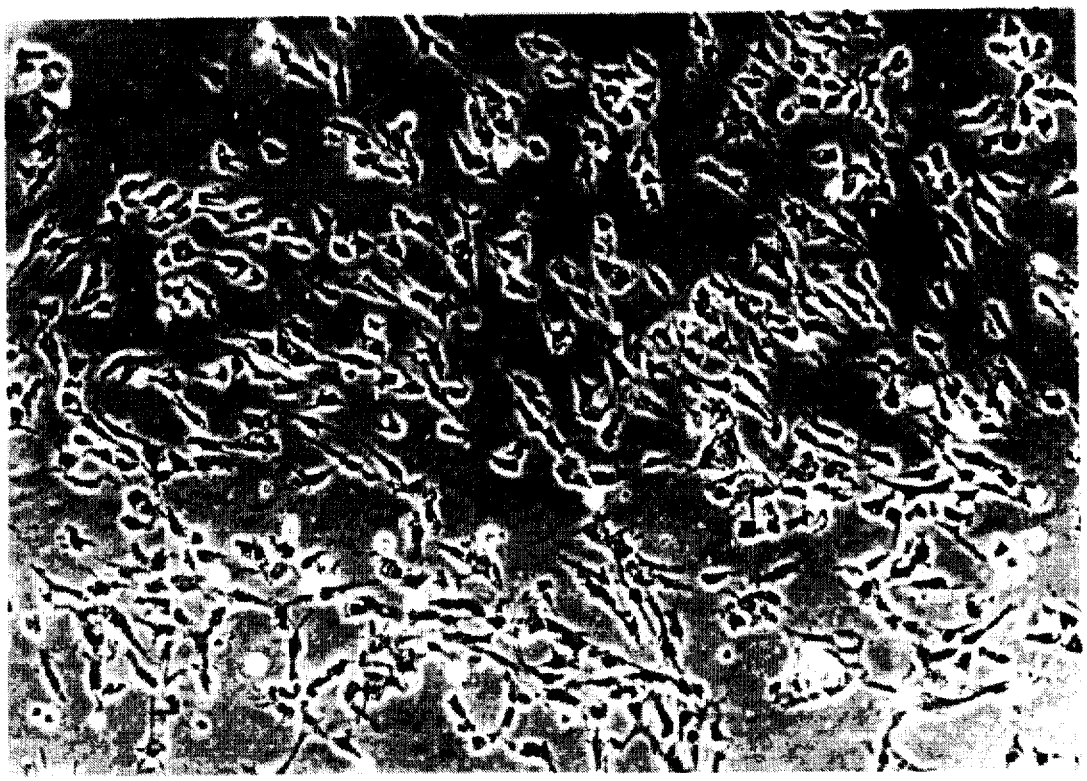
Figure 22C:
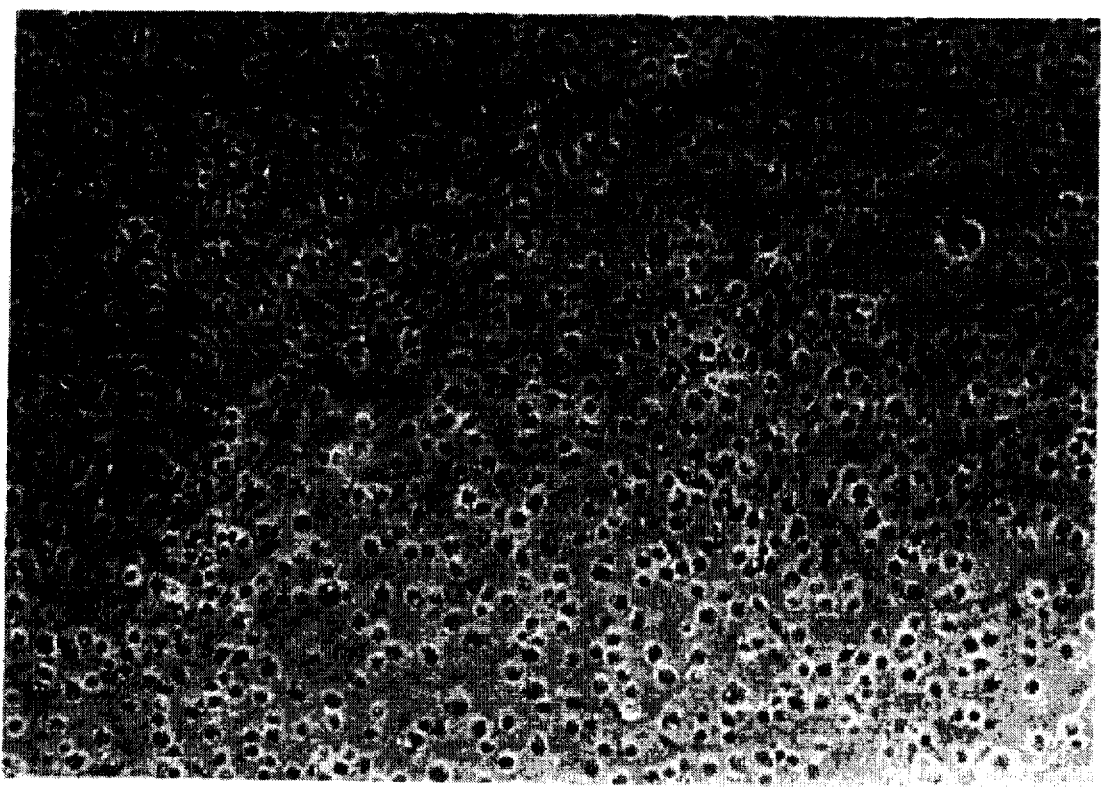

FIG. 22a–c are photographs demonstrating the effect of diffusion distance on cell viability and proliferation: FIG. 22a shows cells from the control well after twenty-four hours, the cell number having doubled in twenty-four hours; FIG. 22b shows cells overlayed with 5.5 mm of 0.32% collagen, showing that the cell viability is markedly diminished and the cell number is far less than the initial plating number; and FIG. 22c shows cells overlayed with 12 mm of hydrated collagen placed between media and cells, showing that all of these cells are rounded and have died.

These data support the concept of diffusion distance being a critical component of cell viability and growth for successful implantation. The concept of uniform cell seeding of a collagen gel is therefore biologically limited by diffusion distance constraints. One would expect that an implant of less than 1 $cm^3$ would result in cell viability at the periphery of the implant to a depth of 3–5 mm. However, the cells in the center of the implant would not remain viable because of limitation of nutrition, diffusion, as well as gas exchange. One can envision large flat gels with very small thicknesses of 5–10 mm would allow larger implants to occur. However, this two dimensional solution may have geometric constraints for implantation. It is also clear that by increasing cell density, diffusion would be more limited, and, therefore, the distances would be commensurately smaller.

Although this invention has been described with reference to specific embodiments, variations and modifications of the method and means for constructing artificial organs by culturing cells on matrices having maximized surface area and exposure to the surrounding nutrient-containing environment will be apparent to those skilled in the art. Such modifications and variations are intended to come within the scope of the appended claims.

We claim:

1. A cell-scaffold composition prepared in vitro for growing cells to produce functional vascularized organ tissue in vivo, comprising:

a fibrous three-dimensional scaffold composed of fibers of a biocompatible, biodegradable, synthetic polymer; and cells derived from a vascularized tissue attached in vitro to the surface of the fibers of the scaffold uniformly throughout the scaffold;

wherein the fibers of the scaffold provide sufficient surface area to permit attachment in vitro of an amount of the cells effective to produce the functional vascularized organ tissue in vivo;

wherein the fibers of the scaffold are spaced apart such that the maximum distance over which diffusion of nutrients and gases must occur through a mass of cells attached to the fibers is between 100 and 300 microns; and wherein the diffusion provides free exchange of nutrients, gases and waste to and from the cells uniformly attached to the fibers of the scaffold and proliferating throughout the scaffold in an amount effective to maintain cell viability throughout the scaffold in the absence of vascularization.

2. The cell-scaffold composition of claim 1 wherein the scaffold is constructed from a material selected from the group consisting of polyanhydrides, polyorthoesters, polyglycolic acid, polymethacrylate, and combinations.

3. The cell-scaffold composition of claim 1 further comprisig a coating on said fibers which enhances cell attachment to the scaffold.

4. The cell-scaffold composition of claim 3 wherein the coating is a material selected from the group consisting of agar, agarose, gelatin, gum arabic, basement membrane material, collagens types I, II, III, IV, and V, fibronectin, laminin, glycosaminoglycans, and mixtures thereof.

5. The cell-scaffold composition of claim 1 wherein the fibers include hollow fibrous members.

6. The cell-scaffold composition of claim 1 wherein the fibers include solid fibrous members.

7. The cell-scaffold composition of claim 1 wherein the scaffold is configured as spicules.

8. The cell-scaffold composition of claim 1 further comprising compounds selected from the group consisting of growth factors, compounds stimulating angiogenesis, immunomodulators, inhibitors of inflammation, and combinations thereof.

9. The cell-scaffold composition of claim 1 wherein the scaffold is configured to provide separate areas of attachment for cells of different origin.

10. The cell-scaffold composition of claim 9 wherein the scaffold is configured such that cell growth forms tubular structures within the scaffold.

11. The cell-scaffold composition of claim 1 comprising separate areas within the scaffold constructed to maximize attachment an growth of different cell populations.

12. The cell-scaffold composition of claim 1 in which the scaffold has a branching structure.

13. The cell-scaffold composition of claim 1 in which the cells are hepatocytes.

14. The cell-scaffold composition of claim 1 in which the cells are bone forming cells.

15. The cell-scaffold composition of claim 1 in which the cells are muscle cells.

16. The cell-scaffold composition of claim 1 in which the cells are intestinal cells.

17. The cell-scaffold composition of claim 1 in which the cells are kidney cells.

18. The cell-scaffold composition of claim 1 in which the cells are lymphatic vessel cells.

19. The cell-scaffold composition of claim 1 in which the cells are blood vessel cells.

20. The cell-scaffold composition of claim 1 in which the cells are pancreatic islet cells.

21. The cell-scaffold composition of claim 1 in which the cells are thyroid cells.

22. The cell-scaffold composition of claim 1 in which the cells are cells of the adrenal-hypothalamic-pituitary axis.

\* \* \* \* \*

UNITED STATES PATENT AND TRADEMARK OFFICE
CERTIFICATE OF CORRECTION

PATENT NO.   : 5,759,830
DATED        : June 2, 1998
INVENTOR(S)  : Joseph P. Vacanti and Robert S. Langer It is certified that error appears in the above-identified patent and that said Letters Patent is hereby corrected as shown below:

Title page, [*] Notice, delete patent number " 5,567,712 "

and insert  --5,567,612--

Signed and Sealed this

Twenty-seventh Day of October, 1998

Attest:

BRUCE LEHMAN

Attesting Officer

Commissioner of Patents and Trademarks